US007404814B2

(12) United States Patent
Shiraishi et al.

(10) Patent No.: US 7,404,814 B2
(45) Date of Patent: Jul. 29, 2008

(54) INFUSION VESSEL

(75) Inventors: Yasuyuki Shiraishi, Chiba (JP); Keiji Hamamoto, Yoyono-gun (JP); Masaharu Nakao, Shiga (JP); Makoto Kuroki, Osaka (JP); Seiji Yoshimura, Osaka (JP)

(73) Assignee: Taisei Kako Co., Ltd., Osaka (JP)

( * ) Notice: Subject to any disclaimer, the term of this patent is extended or adjusted under 35 U.S.C. 154(b) by 238 days.

(21) Appl. No.: 10/307,729

(22) Filed: Dec. 2, 2002

(65) Prior Publication Data

US 2003/0105448 A1 Jun. 5, 2003

(30) Foreign Application Priority Data

Dec. 3, 2001 (JP) ............................ 2001-368141

(51) Int. Cl.
*B65D 25/00* (2006.01)
*B65D 25/04* (2006.01)
*A61B 19/00* (2006.01)

(52) U.S. Cl. ....................... 604/416; 206/221; 220/501; 220/529

(58) Field of Classification Search ................. 604/403, 604/411, 415, 416, 82, 89, 91; 206/363-366, 206/221, 219; 222/129, 145.5, 142.9, 144; 220/501, 529
See application file for complete search history.

(56) References Cited

U.S. PATENT DOCUMENTS 3,441,179 A 4/1969 Ragan
4,623,334 A 11/1986 Riddell
4,727,985 A * 3/1988 McNeirney et al. ......... 206/221
4,735,608 A 4/1988 Sardam
4,903,865 A * 2/1990 Janowitz .................... 222/83.5
5,060,791 A 10/1991 Zulauf
5,088,627 A * 2/1992 Musel ...................... 222/145.5
5,509,530 A * 4/1996 Wilson ....................... 206/220
5,613,623 A * 3/1997 Hildebrandt ................ 222/129
5,685,846 A * 11/1997 Michaels, Jr. ................ 604/90
5,875,889 A * 3/1999 Albisetti ..................... 206/221
6,019,752 A 2/2000 Sunago et al.
6,293,433 B1 * 9/2001 Joulia ......................... 222/129

FOREIGN PATENT DOCUMENTS

EP 0333541 2/1989
EP 0994036 A1 8/1999
GB 391064 11/1932

* cited by examiner

*Primary Examiner*—Leslie R Deak
(74) *Attorney, Agent, or Firm*—Wood, Phillips, Katz, Clark & Mortimer

(57) ABSTRACT

An infusion vessel has a vessel body having an internal cavity to serve as an infusion medium space, a cylindrical discharge mouth continuing from a lower portion of the vessel body, a medicine chamber disposed in the discharge mouth and kept airtight against ambient air, and a separator intervening between the infusion medium space and the medicine chamber so as to keep the space in a liquid-tight state against the holder. The separator is subject to displacement, rotation or deformation such as to bring the infusion medium space into communication with the medicine chamber, so that the infusion vessel can be made ready for use by conducting a simple operation to mix the medicine with the infusion medium that have been separated from each other within the vessel during its normal state before use.

10 Claims, 22 Drawing Sheets

INFUSION VESSEL

FIELD OF THE INVENTION

The present invention relates to an infusion vessel such that a medicine is accommodated therein together with but separated from an infusion medium, so that the medicine will be intermixed with the medium whenever making a liquid for use in infusion treatments.

BACKGROUND OF THE INVENTION

Instillation is carried out often in such a manner that a medicine to be dosed will be mixed previously with an infusion medium such as a physiological saline solution, a glucose solution, a Ringer's solution or an amino acid solution. Many of the medicines used for instillation are chemically unstable in their dissolved state, so that each medicine selected will usually be supplied into the infusion vessel just before instillation.

In one case of dosing a liquid medicine by instillation, it will be sucked at first from a vial into a syringe and then transferred into an infusion vessel. In another case, the vial will be connected by a double-headed needle or by a connection tube to the vessel so as to blend the liquid medicine with an infusion medium. If any powdery, any granular or any freeze-dried medicine is involved, an amount of the infusion medium will be supplied into a vial in order to prepare a solution or dispersion of such a medicine. Subsequently, a syringe, a double-headed needle or a connection tube will be used to transfer the content of this vial to the infusion vessel in the described manner.

However, the infusion liquid will possibly and undesirably be contaminated with foreign substances, alien matters, various germs or sundry bacteria. Such an accident will take place when and while a medicine is sucked from a vial into a syringe, or transferred therefrom to an infusion vessel, or the vial is kept in communication therewith through a double-headed needle or a connection tube.

It will require much time to mix just before instillation any desired medicine with the infusion medium in the described intricate manner, particularly in a case wherein a powdery or freeze-dried medicine is involved. Once intermixed with the medium, the medicine will no longer be identified visually by the appearance of an infusion liquid thus prepared. Therefore, the name of medicine contained in such a liquid (or the name of a patient to whom instillation has to be conducted) is usually marked on the infusion vessel. It also is to be noted that any incorrect marking may be done, unintentionally when or after the infusion liquid is prepared.

SUMMARY OF THE INVENTION

The present invention was made in view of these inconveniences and problems inherent in the prior art. An object of the present invention is therefore to provide an improved infusion vessel designed such that a medicine and an infusion medium (such as a solvent) can be mixed with each other, readily and easily prior to use. Infusion liquid thus prepared has to be of a good conservative property on one hand, and the infusion vessel has to be convenient to handle on the other hand.

In order to achieve the object, an infusion vessel provided herein may comprise a vessel body having an internal space in which an infusion medium is reserved, and a discharge mouth continuing from a lower portion of the vessel body. The discharge mouth may have medicine chamber therein. The medicine chamber may be disposed in the discharge mouth and kept airtight against ambient air. This vessel may further comprise a separator intervening between the internal space of the body and the medicine chamber so as to keep the chamber liquid-tightly relative to the space. The separator may be capable of operating so as to link the internal space to the medicine chamber. The operating of the separator implies displacement, rotation and deformation. The separator may have to be subject to displacement, rotation or deformation such as to bring the internal space into a fluid communication with the medicine chamber. Preferably, the separator may be a member that keeps the internal space not only liquid-tight but also airtight against the medicine chamber so that any amount of air is not allowed to flow between the said space and holder. A handling cap of this infusion vessel may be formed of any proper plastics.

In use, any medicine to be dosed will be stored in a sterilized state within the medicine chamber that is disposed in the discharge mouth itself of the infusion vessel. The airtight chamber will protect the medicine from contamination with bacteria floating within the ambient air. Until usage of this infusion vessel, the medicine in the chamber will be kept off the infusion medium (solvent) stored in the medium space, thus improving conservative property of the medicine. The medicine to be dosed may either be solid (powdery, granulate or freeze-dried) or liquid.

However, the separator will be displaced, rotated or deformed when this infusion vessel is used, to thereby cause the medicine to be mixed with (dissolved or dispersed in) the medium. Displacement of the separator may be effected relative to the vessel body and/or the medicine chamber, and desirably, longitudinally of the discharge mouth or in any other direction. Likewise, rotation of the separator may be effected relative to the vessel body and/or the medicine chamber, and desirably around the discharge mouth or in any other angular direction. On the other hand, deformation of the separator may take place either in all or in some of its component portions, whether elastically or plastically.

The infusion vessel of this invention will be put on market in such a state that its vessel body has clear markings on it as to the type of infusion medium and the sort of medicine. Wrong medicines will no more be added to an infusion medium, thus avoiding the problems and accidents that have been likely to happen in the prior art devices.

The vessel may further comprise a rubber stopper which an instillation needle can pierce. The stopper may be inserted into the external (lower) end of discharge mouth and serving to keep airtight the vessel at said end. This needle communicating with an instillation tube or the like will operate when conducting infusion through it, without any fear of contaminating the interior of said mouth with foreign substances and/or various bacteria. The handling cap may firmly fit on the rubber stopper at said end of discharge mouth.

In one of preferable mode of the invention, the discharge mouth may comprise a medicine holder having an axis and the medicine chamber formed therein, and the handling cap capable of rotation around the axis but incapable of displacement along the axis. The separator may be a rubber stopper that is liquid-tightly fitted in an internal (upper) open end of said medicine holder so as to face the vessel body. A cam mechanism may be disposed in between the handling cap and the separator so that rotation of said cap causes the separator to make an axial movement away from the internal open end. The separator will thus be caused to make an axial movement away from the open end of the medicine holder, thereby bringing the infusion medium space into communication with the medicine chamber.

In this mode of the invention, the rubber stopper serving as the separator will surely keep the medicine chamber off the medium space until use of the infusion vessel. When using this vessel, the cap can be rotated lightly to displace the rubber stopper against a considerably strong sliding resistance acting on it. In this way, the infusion medium space will communicate with the medicine chamber so that the medicine is mixed with the infusion medium. The handling cap may be formed integral with the first mentioned rubber stopper fitted in the distal end of discharge mouth. Rotation of the cap can take place only in unison with this rubber stopper, and frictional resistance against it will inhibit this cap from making an unintended rotation.

The cam mechanism may be of any proper structure, and in a preferable example, a cam will be formed around the handling cap so that a rod extending from the separator engages with the cam. In this case, rotation of the handling cap will force the cam to press a rod-shaped cam follower axially thereof and to thereby move the separator also in axial direction. Alternatively, a cam can be formed on and around the separator, with a rod of the cap contacting the cam. Further, alternatively, a plastics cam may be disposed integral with the rubber stopper to be fitted in the distal end of discharge mouth. Rotation of the handling cap will cause the cam to rotate, which cam in turn will drive the separator in axial direction. Desirably in this case, the separator capable of axial movement is formed not to make any rotational movement.

In the infusion vessel having the described cam mechanism, the rubber stopper may be attached to the handling cap. The rubber stopper is fitted in the end of discharge mouth. The cam mechanism in this case may comprise a plastics cam and a base. The cam may be fixed to the rubber stopper. The base may be engaged with the cam so as to be driven axially and inward when the cam rotates in connection with rotational operation of the handling cap. The separator may be attached to the base not to be removed therefrom in axial direction.

Alternatively, but also in the infusion vessel having the described cam mechanism, its cam may be formed integral with the handling cap. In addition to this cam, a base engaging with it will be installed in this vessel so as to be driven axially and inward when the cam rotates in connection with rotational operation of the cap. The separator also attached to the base will not be removed therefrom in axial direction.

In another alternative example, the cam mechanism may comprise a base having a cam formed therein and engaging the cap. The separator may be secured to the base so as not to be removed axially therefrom, such that rotational operation of the cap will cause the base to move axially inward. A concave region functioning as the cam may preferably be formed in a region of the base so as to open downwards, preventing any residual amount of infusion liquid from remaining in or close to the cam region.

In another preferable mode of the invention, the discharge mouth may comprise a medicine holder having an axis and the medicine chamber formed therein, and the handling cap capable of rotation around this medicine holder and also capable of displacement along the axis. Either the medicine holder or the cap may have a helical portion to keep them in engagement with each other so that the cap moves axially as it rotates. The separator may be a rubber stopper that is fitted liquid-tightly (more preferably, liquid-tightly and air-tightly) in an internal (upper) open end of said medicine holder so as to face the vessel body. Rotational operation of said cap will cause the separator connected thereto to move axially away from the internal open end of the medicine holder, thereby linking the internal space to the medicine chamber. Also in this mode, the rubber stopper serving as the separator will surely keep the medicine chamber off the medium space until use of the infusion vessel. When using this vessel, the cap can be rotated lightly to displace the rubber stopper against a considerably strong sliding resistance acting on it. In this way, the medium space will communicate with the medicine chamber so that the medicine is surely intermixed with the infusion medium.

The handling cap may either fit in or fit on the medicine holder serving as or having the medicine chamber formed therein. In any case, either the medicine holder or the handling cap has the helical portion to keep them in engagement with each other so that the cap is allowed to move axially as it rotates. The rubber cap at the distal end of discharge mouth may be fitted air-tightly in the handling cap. The axial movement of the medicine holding medicine holder may not break airtight-ness thereof (viz., airtight-ness of the medicine chamber against the ambient air) when the cap rotates. A connector may be incorporated in this vessel so as to connect the cap to the separator so as not to be removed therefrom in axial direction.

In a further alternative mode, the discharge mouth may comprise a medicine holder having an axis and a support member. The medicine holder may be connected to the support member so as to be capable of inward displacement along the axis. The medicine holder may have said medicine chamber flared up outwards in axial direction. The medicine holder may comprise a sealing cylinder to liquid-tightly (more preferably, liquid-tightly and air-tightly) fit on a rubber stopper as the separator. The support member may be formed integral with the vessel body. Movement of the medicine holder towards the support member will cause the separator located in the sealing cylinder to move towards the flared region of the medicine holder. As a result, the medicine chamber will communicate with the infusion medium space, through the interior of support cylinder. More preferably, the cylindrical medicine chamber may be designed such that the rubber stopper at the open end of discharge mouth will fit air-tightly on another end located axially opposite to the one end facing the vessel body. This vessel may further comprise a connection cylinder secured on the cylindrical medicine chamber and capable of axially sliding relative to the support cylinder in an airtight manner. In this case, as the cylindrical holder pushed inwards shifts its position towards the support cylinder, this cylinder will air-tightly move along the inner periphery of the connection cylinder. Consequently and similarly to the first case mentioned above, the separator in the sealing cylinder will advance towards the flared region of medicine chamber.

It is an advantage of this structure that a simple pushing of the cylindrical medicine chamber towards the support cylinder does suffice well to bring the medium space into fluid communication with the medicine chamber so that the medicine is mixed with the infusion medium. The rubber stopper serving as the separator mentioned above will reliably keep the medicine chamber separated from said medium space, until use of this infusion vessel.

Preferably, a spacer may be detachably attached to the outer periphery of support cylinder so that the medicine chamber is inhibited from displacement towards the support cylinder for communication therewith. This is for the purpose of preventing any unintentional communication of said holder with said medium space during storage and transportation of the vessel. However, when using it, the spacer will easily be taken off the support cylinder so that the medicine chamber is ready to be pushed in towards this cylinder and brought into communication with the medium space.

A releasable detent (or latch) may substitute for such a spacer as just summarized above, in order to hold the medicine chamber at its inoperative position until it is forced to take its operative position when using this infusion vessel. In detail, if an external force strong enough to overcome the detent for retention of the medicine chamber is applied, then it will become able to be driven towards the support cylinder so as to rest at its operative position and not to be unintentionally displaced therefrom.

The spacer mentioned above may be replaced with a proper interlock mechanism such that the medicine chamber is inhibited from axial movement whether or not it has been pushed inwards. For example, manual rotation of the medicine chamber by a predetermined angle will be effective to surely lock its axial motion, such that it will selectively be held at its operative position or at its inoperative position.

The separator as discussed above may be composed of a partition and a sealing member, wherein the partition has an aperture or apertures for linking the medium space of the body to the medicine chamber. The sealing member may cause the aperture to remain closed at its end opened into the internal space. And, the aperture or apertures may remain closed at its end facing the interior of medium space, by means of this sealing member. The discharge mouth may comprise correspondingly and in addition to the handling cap capable of rotational operation, and a releaser. The releaser may be capable of deforming the sealing member so as to open the aperture in connection with rotational operation of the cap. The thus opened aperture enables a fluid communication between the medium space and the medicine chamber. A self-sealing effect is thus afforded by such a sealing member to which a static hydraulic pressure of infusion medium will act towards the aperture's opening facing the interior of said space, thereby improving liquid-tightness.

A thin film may be used as the sealing member that will be bonded to the partition by means of a plastics adhesive, so as to close the aperture formed in said partition in such a manner that it can be opened later in use. Alternatively, a thin plastics layer may be laminated on a pre-molded partition, or a thermally shrinking film may be placed on the partition and then heated to temporarily cover and close the aperture.

The releaser referred to above may be composed of a group of elastic vanes each extending outwards and radially from a rotation axis of the handling cap. In this case, a peripheral wall is formed in the partition, with the aperture being defined by and through this peripheral wall. If the handling cap is driven to twist, then these vanes in contact with said wall will deform themselves elastically while advancing into the aperture. Due to elastic recovery in shape of each vane, the sealing member will be deformed and opened in part.

Elastic protrusion of those vanes will surely cause deformation of the sealing member away from the aperture in close contact with it, thus avoiding any incomplete communication of the space with the medicine chamber. The term 'deformation' used with respect to the sealing member in the present invention denotes inclusively the partial elongation or partial breakage of the sealing member. Elongation is preferred, since breakage of the sealing member will produce minute fragments thereof unless it is made of a special non-fragile material.

BRIEF DESCRIPTION OF THE DRAWINGS

FIG. 1(*b*) is a vertical cross section of a discharge mouth which the infusion vessel shown in FIG. 1(*a*) does comprise;

FIGS. 2(*b*) and 2(*c*) are perspective views of the cam mechanism shown in its operation;

FIG. 3(*b*) is a vertical cross section of the infusion vessel shown in FIGS. 1(*a*) and 1(*b*), wherein its medicine chamber has been brought into communication with its medicine chamber;

FIG. 4(*b*) is a vertical cross section of a discharge mouth which the infusion vessel shown in FIG. 4(*a*) does comprise;

FIGS. 5(*b*) and 5(*c*) are perspective views of the handling cap being rotated during its operation;

FIG. 6(*b*) is a vertical cross section of the infusion vessel shown in FIGS. 4(*a*) and 4(*b*), wherein its medicine chamber has been brought into a fluid communication with its medicine chamber;

FIG. 7(*b*) is a vertical cross section of a discharge mouth which the infusion vessel shown in FIG. 7(*a*) does comprise;

FIG. 8(*b*) is a vertical cross section of the infusion vessel shown in FIGS. 7(*a*) and 7(*b*), wherein its medicine chamber has been brought into communication with its medicine chamber;

FIG. 9(*b*) is a vertical cross section of a discharge mouth which the infusion vessel shown in FIG. 9(*a*) does comprise;

FIG. 9(*c*) is a cross section taken along the line A-A in FIG. 9(*b*);

THE PREFERRED EMBODIMENTS

Figure 1A:
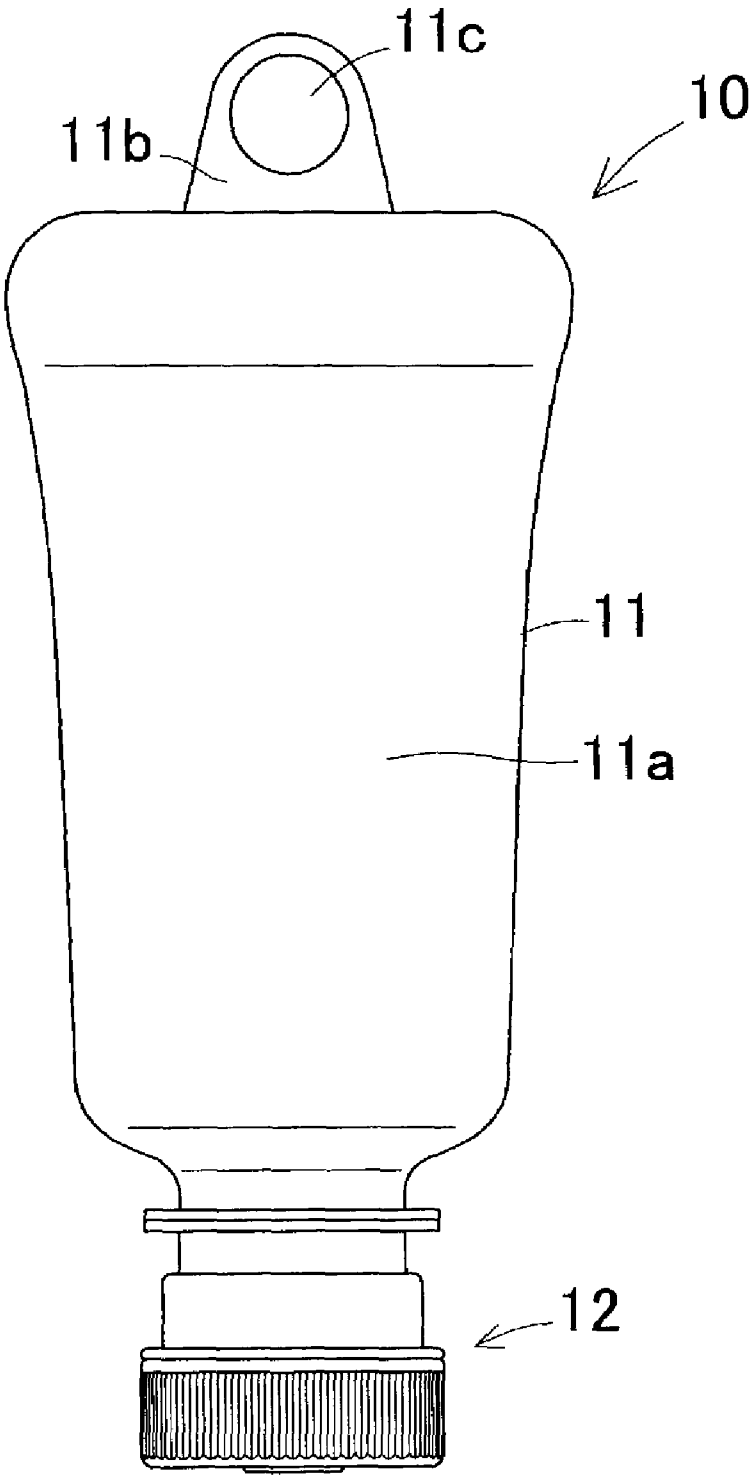
FIG. 1(*a*) is a front elevation of an infusion vessel provided in a first embodiment of the present invention.

Now some embodiments of the present invention will be described referring to the drawings.

Figure 1B:
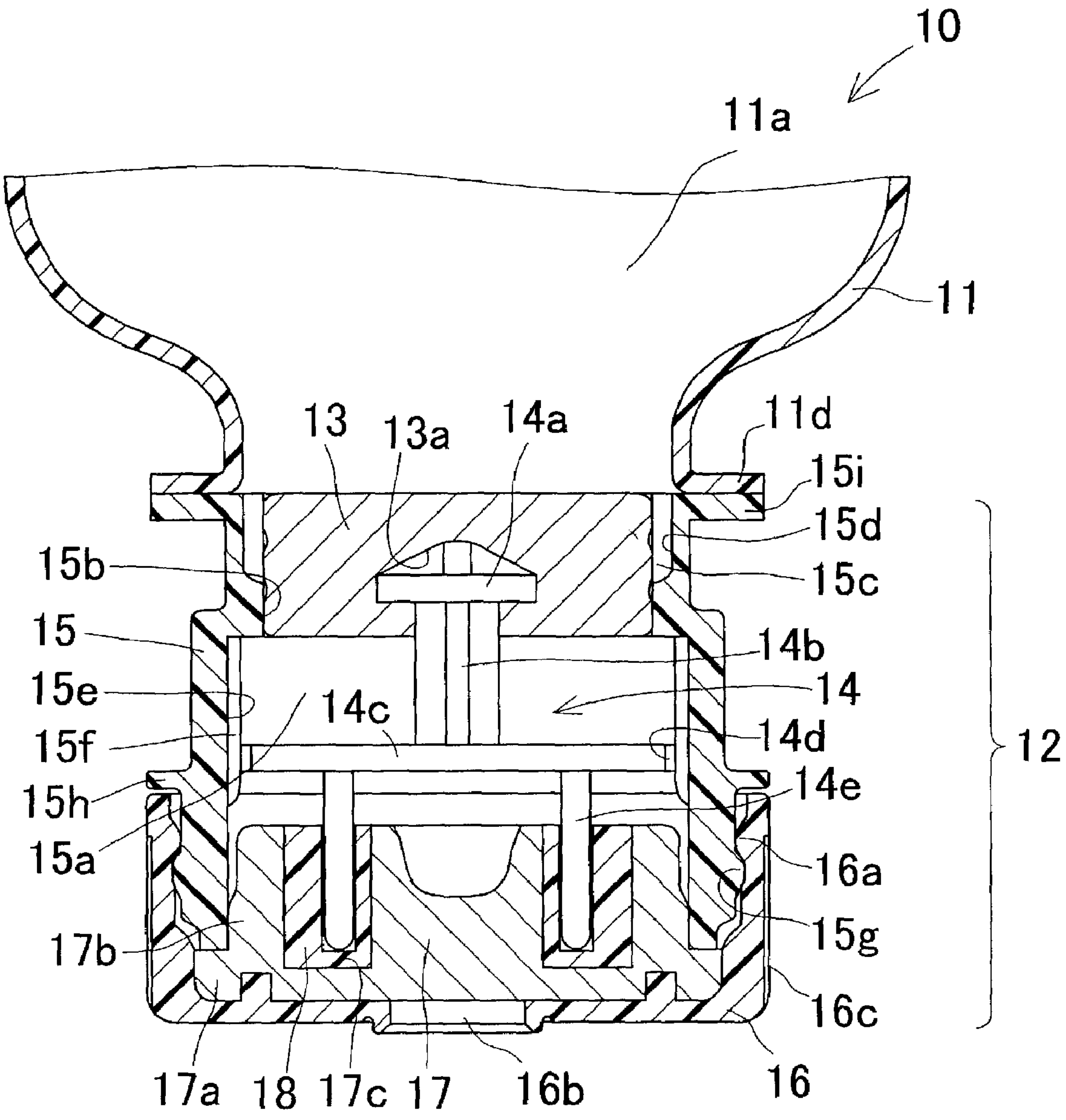

FIGS. 1(*a*) to 3(*b*) shows an infusion vessel 10 that is provided in a first embodiment of the present invention (particularly as set forth in the accompanying claim 4). The infusion vessel 10 comprises a vessel body 11 that may be a flexible bag or a rigid vessel, whose internal space 11*a* serves as an infusion medium reservoir. A cylindrical discharge mouth 12 extends from the lower end of the vessel body 11. An eyed tab 11*b* formed integral with the upper end of this body 11 has a hole 11*c* to be hooked to hang the vessel 10. A rim around the lower end opening of said body 11 is bent outwards and radially to provide a flange 11*d*. A medicine chamber 15*a* is formed in the discharge mouth 12, and a stopper (separator) 13 intervenes between this holder 15*a* and the infusion. The stopper 13 normally keeps the medicine chamber 15*a* liquid-tight and airtight against the medium space 11*a*.

In a case wherein the vessel body 11 is a bag, it may be formed of any proper flexible material such as polyvinyl chlorides and polyolefin resins. Among a variety of polyolefin resins, polyethylene and polypropylene are preferable because they are highly resistant to chemicals and less likely to migrate into the infusion medium. However, the vessel body 11 may alternatively be formed as a bottle-like article.

As shown in FIG. 1(*b*), the discharge mouth 12 comprises a base 14 for supporting the stopper 13 and a medicine holder 15 serving as or having formed therein a medicine chamber 15*a*. A handling cap 16 is rotatably mounted on the medicine holder 15. A cam mechanism intervenes between the cap 16 and separator 13, such that rotation of the handling cap 16 will cause axial displacement of the separator 13 in a direction away from the end opening of said vessel body 11. A rubber stopper 17 secured in the handling cap 16 is incapable of rotation relative thereto. A hard resin cam (plastics cam) 18 as one component part of the cam mechanism is firmly secured in the rubber stopper 17.

As seen in FIGS. 1(*b*) to 2(*c*), the stopper 13 is a generally columnar piece that is made of a butyl rubber to have a central bore 13*a* with a closed bottom and fitting on a part of the base. This bore 13*a* does not penetrate the stopper 13, but is opened only downwards (viz., downstreamly of the medium being discharged).

As shown also in FIGS. 1(*b*) to 2(*c*), the base 14 is composed of several portions. These portions are: an end rod 14*a* engaging with the central bore 13*a* , an intermediate rod 14*b* extending down from the end rod 14*a* , a slide plate 14*c* whose center is integral with the lower end of intermediate rod 14*b* , and two elongate cam rods 14*e* with lengths protruding down in the cantilever fashion from the slide plate and each terminating at an end. The end rod 14*a* is incapable of removing in axial direction from the stopper 13, with the slide plate 14*c* being shaped as if opposite crescent regions would have been severed off a round plate. Such a base 14 may be made for example by injection of a high-density polyethylene resin.

The diameter of an imaginary circle circumscribed about the slide plate 14*c* is slightly smaller than the inner diameter of a lower enlarged region (detailed later) of cylindrical medicine chamber 15. Slide grooves 14*d* are formed in the middle portions of opposite arcuate edges of the slide plate, thus being disposed symmetrical with each other about the center of said plate 14*c*.

The medicine chamber 15 is cylindrical and has in its upper region a sealing portion (viz., round end opening) 15*b* to fit on the periphery of stopper 13 in a liquid-tight and airtight state. The lower enlarged region 15*e* referred to above and continuing down from the sealing portion 15*b* has a diameter larger than the sealing portion. A rim around the upper end of said portion 15*b* is bent outwards and radially to provide a further flange 15*i*. Such a cylindrical medicine chamber 15 may be made for example by injection of a suitable thermoplastics such as polypropylenes.

Under a natural condition of the sealing portion 15*b* not yet fitted on the stopper 13, it has been of a diameter slightly larger than the diameter of this stopper. Thus, an airtight and liquid-tight sealing is ensured between the said portion 15*b* and said stopper 13 fitted therein.

A further or upper enlarged region 15*d* continuing up from the sealing portion 15*b* has an increased inner diameter as compared with this portion. A plurality of ridges 15*c* extending in axial direction of medicine chamber are formed integral with the inner periphery of the upper enlarged region 15*d*. The inner diameter of this region 15*d* is greater a little than the diameter of stopper 13. The inner diameter of an imaginary circle inscribed to include therein all the tops of ridges 15*c* is generally equal to the inner diameter of the sealing portion 15*b*. The stopper 13 can be lifted away from this sealing portion so as to be held in place by the ridges 15*c*, when the present vessel is used. Thus, clearances will appear between the outer periphery of stopper 13 and the inner periphery of upper enlarged region 15*d*, thereby providing liquid communication across this stopper.

Formed on and integral with the inner periphery of lower enlarged region 15*e* are two ribs 15*f* that fit in the respective slide grooves 14*d* formed in the base 14, so as to enable axial movement thereof, while inhibiting rotation thereof. On the other hand, formed integral with the lower part of outer periphery of the lower enlarged region 15*e* is a circular protuberance 15*g* for engagement with the handling cap 16. A shoulder 15*h* also formed on the outer periphery of said region 15*e* but above the circular protuberance 15*g* will stand in contact with the upper annular edge of said cap 16, thereby retaining same at its correct position.

The handling cap 16 is a cylindrical piece with a closed bottom whose central portion is opened to be an aperture 16*b* enabling penetration of a communication needle (not shown) through this cap. Such a handling cap 16 may also be made for example by injection of a suitable thermoplastics such as polypropylenes. The inner diameter of cap 16 is generally the same as the outer diameter of the lower enlarged region 15*e* of cylindrical medicine chamber 15. An-annular ridge 16*a* is formed integral with the inner periphery of this cap 16, and minute anti-slip axial indentations 16*c* are engraved in and around the outer periphery of said cap.

By pressing the handling cap 16 onto the lower enlarged region 15*e* of medicine chamber 15, a part of this cap will be forced into this region. Thus, its annular ridge 16*a* engages with the protuberance 15*g* such that its upper edge is stopped and held in position by the shoulder 15*h* of medicine chamber 15. In this state, the cap 16 can rotate around this holder 15, but cannot move axially thereof.

A rubber stopper 17 has a larger-diameter portion 17*a* to be pressed in the cap 16 as well as a smaller-diameter portion 17*b* fitted in the lower enlarged region 15*e* of medicine chamber 15. The communication needle (not shown) can penetrate this rubber stopper 17 so that an infusion tube will communicate with this vessel 10. The handling cap 16 having such a rubber stopper 17 pressed therein is forced to firmly engage with the holder 15. Its lower enlarged region's edge 15*e* and its inner peripheral portion adjacent thereto are thus brought into a close and pressed contact with the rubber stopper 17, whereby airtight seal is provided between the holder 16 and cap 15. An annular recess 17*c* formed in the stopper 17 and around its axis is for reception of a cam member 18, and a central round recess formed in this stopper will facilitate the pricking of communication needle mentioned above.

Figure 2B:
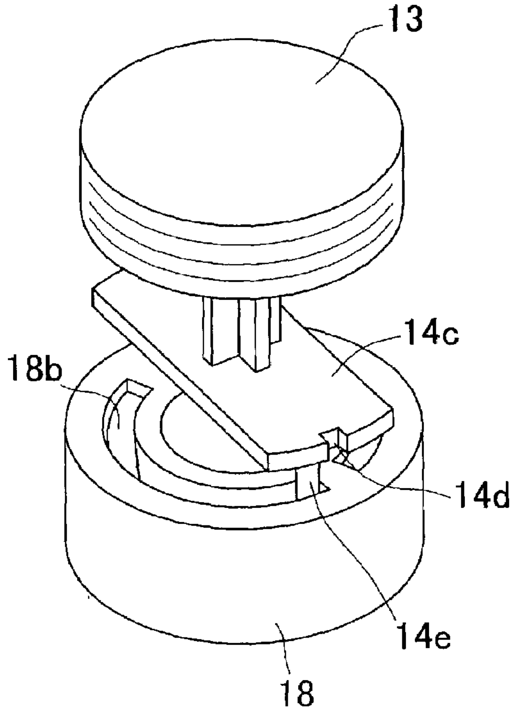
FIG. 2(*a*) is an exploded perspective view of a cam mechanism which the infusion vessel shown in FIGS. 1(*a*) and 1(*b*) does comprise.
Figure 2A:
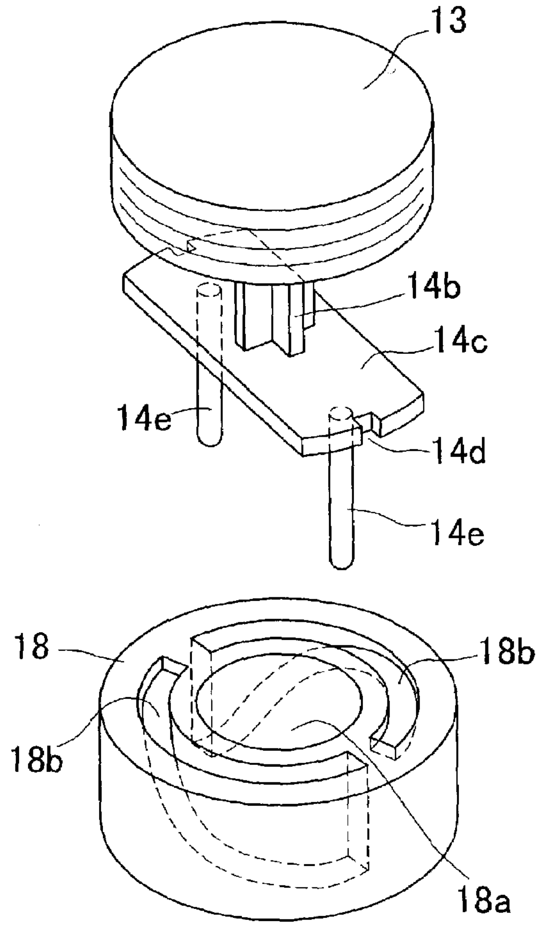
Figure 2C:
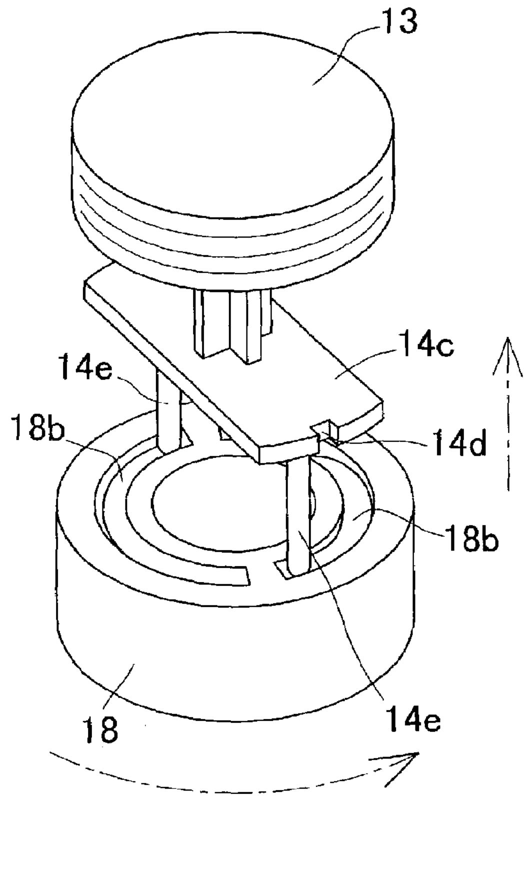

The cam member 18, as seen in FIG. 2(*a*), is of a ring shape having an axial bore 18*a* and has cams 18*b* each between the outer and inner peripheries of such a ring. Such a cam member 18 may also be made for example by injection of a high-density polyethylene resin.

The two cams 18*b* increase their depth gradually in one and the same angular direction along the peripheries of cam member 18 firmly fitted in the rubber stopper's annular recess 17*c*, and they are disposed symmetrically about the axis thereof.

Now, an example of assembling process in manufacture of the infusion vessel is described below, wherein given proper amounts of a liquid medium and a selected medicine will be accommodated in the vessel.

At first, the flange 11*d* of vessel body 11 will be fusion bonded to the flange 15*i* of cylindrical medicine chamber 15, before pouring into the space 11*a* of vessel body 11 the given amount of the medium of an infusion liquid.

The infusion medium to be filled in said space 11*a* may for example be an infusion medium such as a physiological saline solution, a glucose solution, an amino acid solution, a Ringer's solution, a distilled water for injection purpose or any other electrolyte solution.

The thermal fusion method or the ultrasonic welding method may be employed to bond the flange 11*d* to the cylindrical medicine chamber 15.

Subsequently, the end rod 14*a* of base 14 will be fitted in the central bore 13*a* of the first mentioned stopper 13, which stopper then leads the base 14 into the lower enlarged region 15*e* of cylindrical medicine chamber 15. Thus, the slide grooves 14*d* in the base will engage with the respective ribs 15*f* in medicine chamber 15 so that this base 14 is further pressed in until the stopper 13 comes into a close and tight contact with the sealing portion 15*b*. In this way, the medium space 11*a* is sealed with the first mentioned stopper 13.

Next, the medicine chamber 15*a* (viz., the interior of lower enlarged region 15*e*) in discharge mouth's medicine holder 15 will be filled with a given amount of medicine. The handling cap 16 having the rubber stopper 17 and cam member 18 firmly held therein will be fitted in the lower enlarged region 15*e*. The cam rods 14*e* of the base 14 thus disposed in the respective cams 18*b* should have their lower free ends in contact with the deepest bottom portions of said cams, with the annular ridge 16*a* engaging the circular protuberance 15*g*.

The medicine chamber 15*a* thus installed in the vessel is isolated by stopper (separator) 13 from the medium space 11*a* also attached to the vessel. Vessels 10 prepared and finished in the manner described above are now in their state suited to storage and transportation.

The medicines stored in the cylindrical holder 15*a* may be antibiotics, antineoplastic agents, antiulcer agents and the like. Examples of antibiotics are those included in the penicillin antibiotics or the cephem antibiotics. The penicillin antibiotics may include ampicillin sodium, calpenicillin sodium, sulbenicillin sodium, ticarcillin sodium, etc. The cephem antibiotics may include cephazolin sodium, ceftizoxime sodium, cefotiam hydrochloride, cefmenoxime hydrochloride, cephacetrile sodium, cefamandole sodium, cefaloridine, cefotaxime sodium, cefotetan sodium, cefoperazon sodium, cefsulodin sodium, ceftezole sodium, cefpiramide sodium, cefmetazole sodium, cefuroxime sodium, etc. Examples of antineoplastic agents are mitomycin-C, fluorouracil, tegaful, citarabine, etc. Examples of antiulcer agents are ranitidine hydrochloride, famotidine, cimetizine, etc.

An operation for establishing liquid communication between the space and holder, as well as subsequent flow of the infusion liquid, will now be described.

Figure 3A:
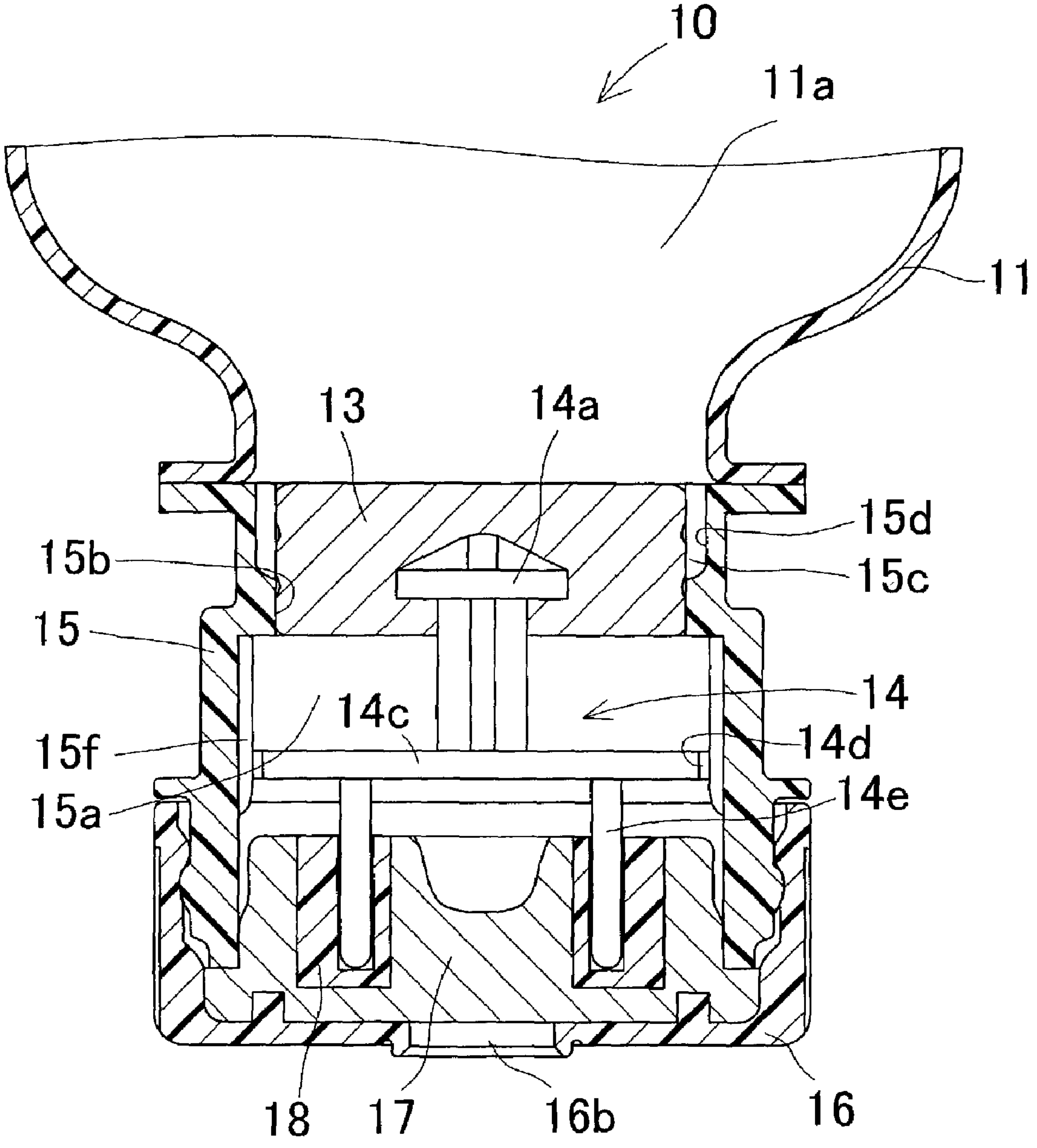
FIG. 3(*a*) is a vertical cross section of the infusion vessel shown in FIGS. 1(*a*) and 1(*b*), wherein its medicine chamber is not in a fluid communication with its medicine chamber.
Figure 3B:
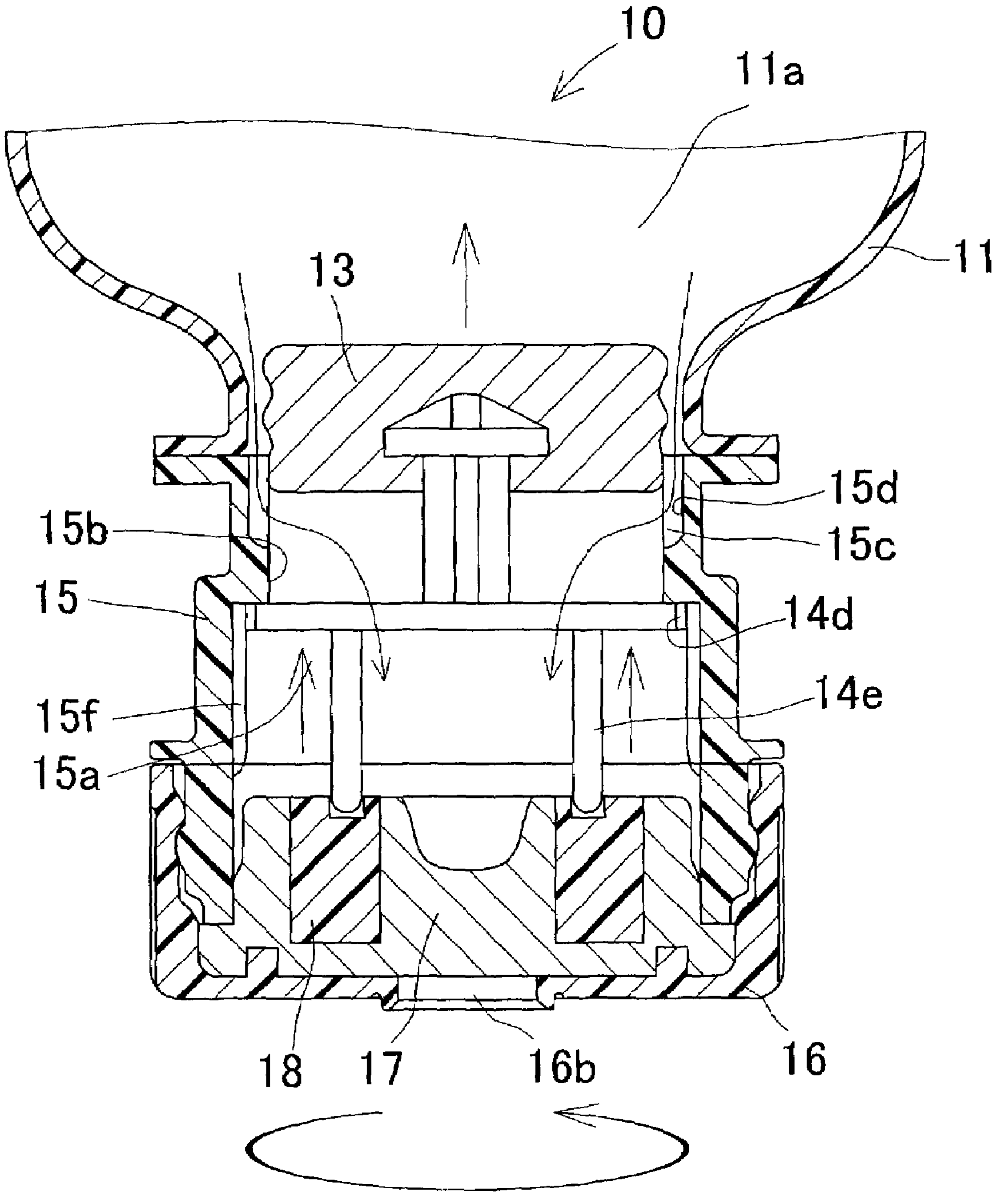

In order to start instillation, the handling cap 16 for the vessel 10 must be driven to circumrotate clockwise (when seen upwards in FIG. 3(*b*) of the drawings). Because the slide grooves 14*d* in the base 14 are in engagement with the ribs 15*f* in medicine chamber 15, this base cannot spin. Thus, oblique surfaces of cams 18*b* will force upwards the cam rods 14*e* formed integral with the base 14, thereby lifting same (in axial direction) as seen in FIGS. 2(*b*) and 2(*c*).

FIG. 3(*b*) shows that as the cap 16 spins a maximum angle to lift the base 14, the stopper 13 will rise and enter the upper enlarged region 15*d* disposed above the sealing portion 15*b* medicine chamber. Clearances thus appearing between the outer periphery of stopper 13 and the inner periphery of enlarged region 15*d* will operate as communication passages for the infusion medium or liquid flowing down from the medium space 11*a* and into the medicine chamber 15*a* of medicine holder.

The handling cap 16 in the infusion vessel 10 of this embodiment is operated to rotate in the described manner. However, the rubber stopper 17 fitted in this cap is kept in a tight contact with the inner periphery of the medicine chamber's lower larger-diameter region 15*e*. In detail, the lower end and a bottom portion adjacent thereto of this region 15*e* will remain pressed with the rubber stopper 17, without any fear of breaking air-tightness between the cap 16 and the medicine chamber 15.

Once such a communication is established, the vessel 10 will be subjected to vibration so as to intermix (dissolve or disperse) the medicine with the infusion medium. A communication needle (not shown) will then be directed through the handling cap aperture 16*b* so as to penetrate the rubber stopper 17, so as to start instillation.

The vessel body 11 will carry some proper markings indicating the kind of infusion medium and the sort of medicine, both having to be confirmed prior to infusion.

Whether the described communication has not yet been established, or just is being or has already been established, the infusion vessel 10 of the present embodiment will never fail to keep airtight both the medicine chamber 15*a* and medium space 11*a*, protecting them from foreign matters or various bacteria. Simple rotation of the handling cap 16 suffices well to blend the medicine with the infusion medium, thereby simplifying works required to perform an infusion treatment and thus avoiding any error that have often resulted heretofore from intricate operations.

Although the slide plate 14*c* of base 14 in this embodiment looks as if opposite crescent regions had been severed off a round plate, the invention is not delimited to such a configuration of the slide plate. Instead, it may be of any other shape such that several openings or cutouts are formed in and arrayed radially of the round plate. In this case, a plurality of circumferential edge portions may be provided around such a plate, corresponding to an increased number of ribs 15*f* formed in the cylindrical medicine chamber 15.

The process exemplified above to assembly the infusion vessel 10 is not intended to delimit the scope of invention. Although the fusion bonding of the medicine holder 15 for holding medicine to the vessel body 11 is carried out at first, this step may be conducted as a final step. In such an alternative case, the base 14 having the stopper 13 secured thereto will be pressed at first into the medicine holder 15 of discharge mouth, and then its medicine chamber 15*a* will be charged with an amount of medicine. The handling cap 15 will subsequently be press-fitted on the mouth, before the medicine holder 15 is finally fusion-bonded to the vessel body 11.

Figure 4A:
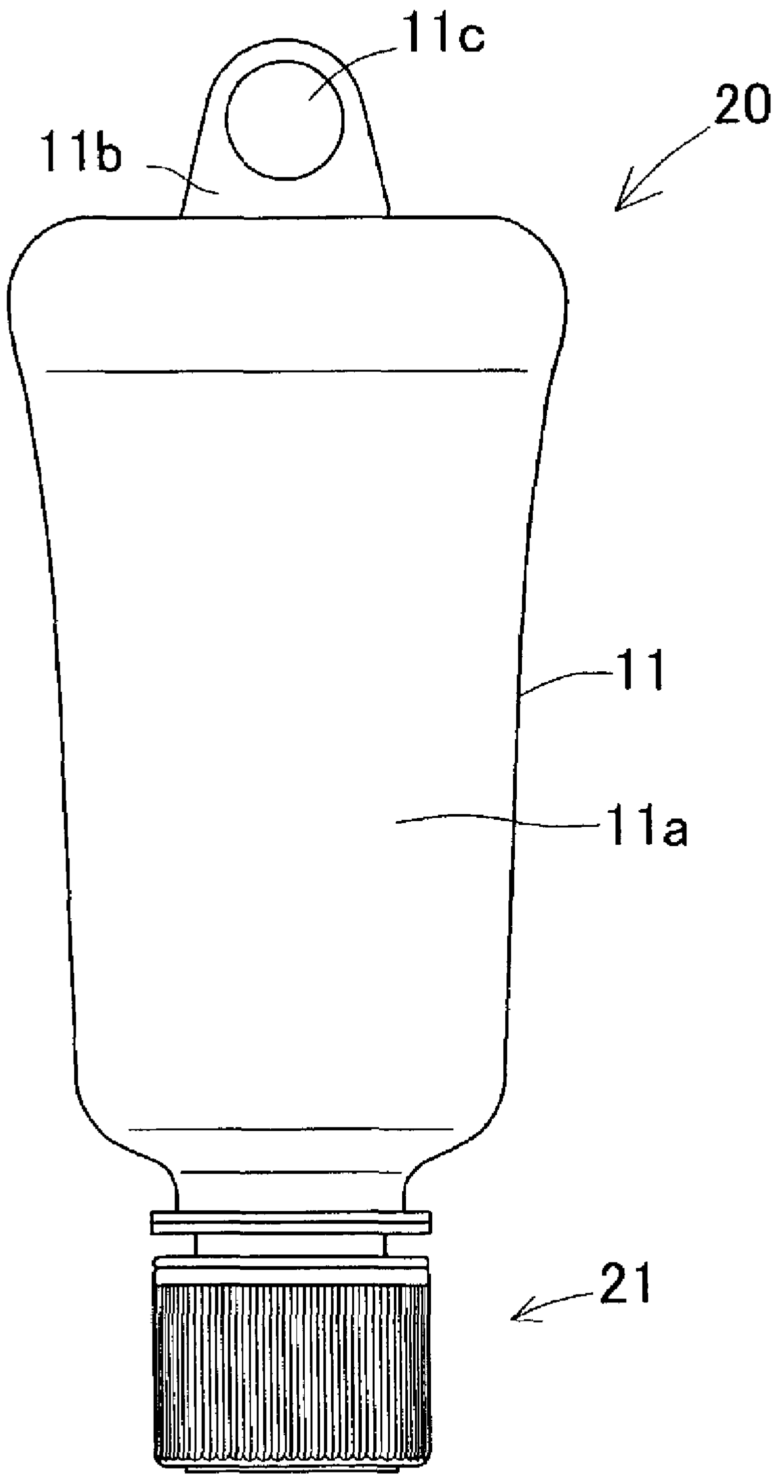
FIG. 4(*a*) is a front elevation of an infusion vessel provided in a second embodiment.
Figure 4B:
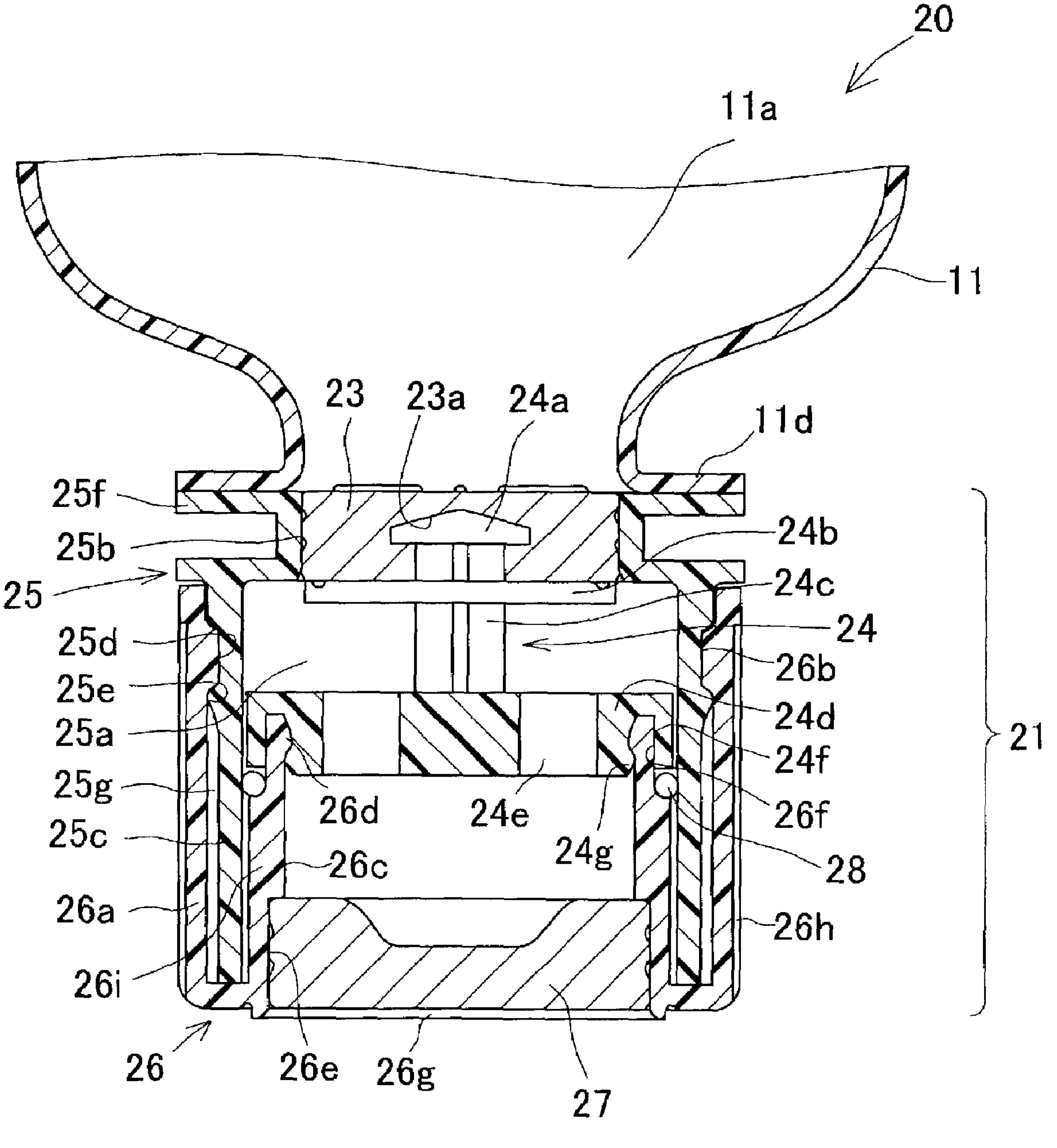

FIGS. 4(*a*) to 6(*b*) show an infusion vessel 10 that is provided in a second embodiment of the present invention (as set forth particularly in the accompanying claim 7). The infusion vessel 20 comprises a vessel body 11 similar to that in the first embodiment, and a cylindrical discharge mouth 21 continues down from the lower end of this vessel body 11.

As seen in FIG. 4(*b*), this discharge mouth 21 is composed of a stopper (separator) 23, a base 24 to which the stopper is to be secured, a medicine holder 25 with a cavity serving as a medicine chamber 25*a*, a handling cap 26, a rubber stopper 27 press-fitted in the cap 26 and an O-ring 28 press-fitted thereon.

The first mentioned stopper 23 is a generally columnar piece of a butyl rubber, and has a central bore 23*a* with a closed bottom and shaped to fit on a portion of the base 24.

This base 24 is composed of an end rod 24*a* for engagement with the bore 23*a* of stopper 23, a flange 24*b* contacting the lower surface of stopper 23, an intermediate rod 24*c* depending down from flange 24*b*, and a considerably short cylindrical support 24*d* continuing down from intermediate rod 24*c*. Such a base 24 may for example be formed by injection of a high-density polyethylene or the like resin.

The outer diameter of cylindrical support 24*d* is slightly smaller than the inner diameter of a larger-diameter region (detailed later) of the medicine holder 25 serving as the medicine chamber. Thus, this support 24*d* can move axially and spin within the medicine-holding medicine holder 25.

The cylindrical support 24*d* has a plurality of communication holes 24*e* formed each in a radial direction. An annular recess 24*f* is formed in the lower peripheral zone of said support 24*d* so as to extend all around it to be fitted on an annular portion of the handling cap 26. An inner peripheral wall defining such a recess 24*f* has an integral annular detent 24*g*, also extending all around this recess.

The medicine holding part 15 is cylindrical and has in its upper region a sealing portion 25*b* to fit on the periphery of stopper 23. The lower enlarged region 25*c* referred to above and continuing down from the sealing portion 25*b* has a diameter larger than the sealing portion. A rim around the upper end of said portion 25*b* is bent outwards and radially to provide a further flange 25*f*. Such a cylindrical medicine chamber 15 may be made for example by injection of suitable thermoplastics such as polypropylenes.

Under a natural condition of the sealing portion 25*b* not yet fitted on the stopper 23, it has been of a diameter slightly larger than the diameter of this stopper. Thus, a liquid-tight sealing will be ensured between the said portion 25*b* and said stopper 23 fitted therein.

Figure 5B:
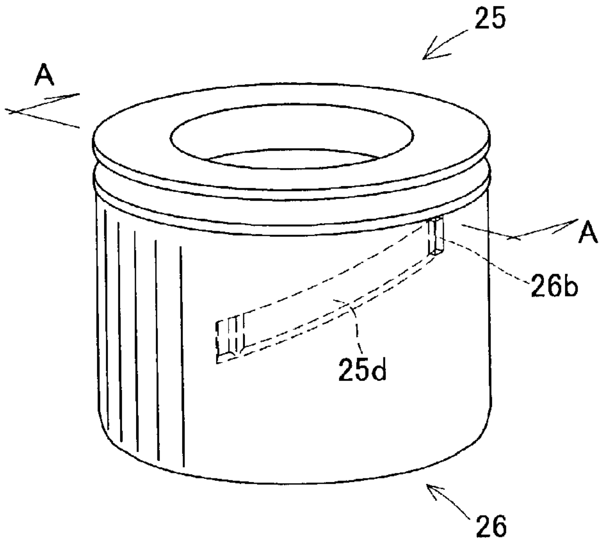
FIG. 5(*a*) is an exploded perspective view of a handling cap in engagement with a medicine holder that is formed as a medicine chamber in the infusion vessel shown in FIGS. 4(*a*) and 4(*b*)
Figure 5A:
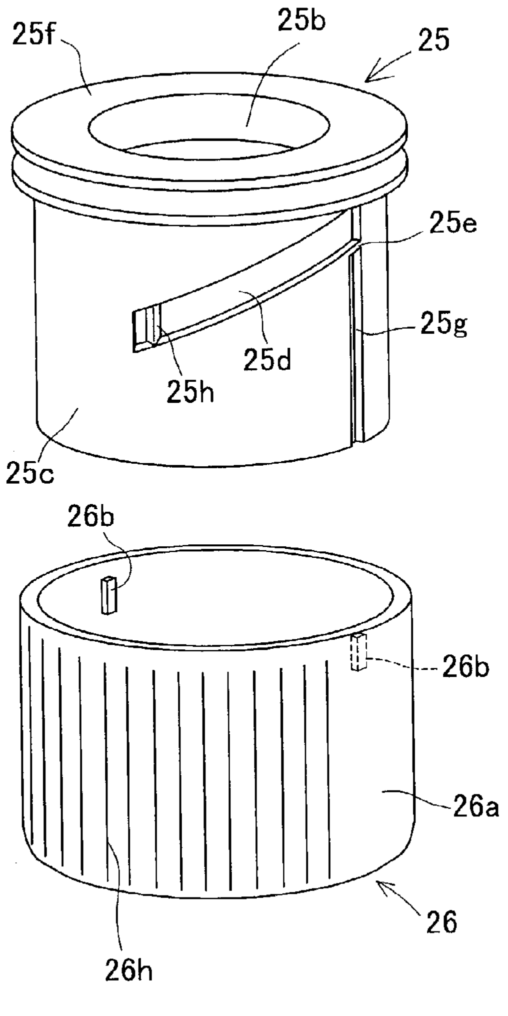
Figure 5C:
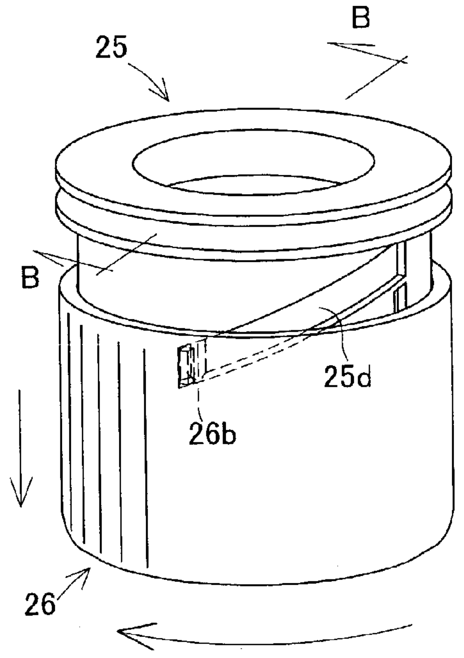

FIG. 5(*a*) shows that slide grooves 25*d* each of a given length are formed in the outer periphery of enlarged region 25*c* in a helical fashion relative to the axis of this region, in order to engage with the handling cap 26. A vertical groove 25*g* continues from the upper end of each helical slide groove 25*d* so as to extend substantially over the full height of enlarged region 25*c*. The lower end of each slide groove 25*d* has a bottom portion bulged up to provide a lug 25*h*. Two pairs of such a helical groove 25*d* and such a vertical groove 25*g*, both formed in the outer periphery of enlarged region 25*c*, are arranged symmetrical with each other about the axis of this region.

The handling cap 26 formed of a polypropylene or the like proper thermoplastic resin is generally composed of a cap body 26*a* and an inner cylinder 26*i*. The cap body 26*a* is fitted on the outer periphery of enlarged region 25*c* of the cylindrical medicine chamber 25, with the inner cylinder 26*i* being engaging with the cylindrical support 24*d* of base 24. A full opening 26*g* is formed in the bottom of this cap 26 so as to be press-fitted on a rubber stopper 27.

As seen in FIG. 5(*a*), the inner periphery of cap body 26*a* has two lugs 26*b* formed integral with its upper portion. The lugs 26*b* arranged symmetrical with each other about the axis of this cap are engagement with the respective slide grooves 25*d* of cylindrical medicine chamber 25. Minute anti-slip vertical indentations 26*h* are formed in the outer periphery of cap body 26*a*.

On the other hand, the inner cylinder 26*i* is almost of the same outer diameter as the short cylindrical support 24*d* of base 24. The peripheral wall of the enlarged region 25*c* of cylindrical medicine chamber 25 will thus be fitted in between the outer periphery of inner cylinder 26*i* and the inner periphery of cap body 26*a*.

The inner cylinder 26*i* is composed of an upper smaller-diameter portion 26*c* and a lower larger-diameter portion 26*e* formed integral therewith. The top of such a smaller-diameter portion 26*c* has an annular lug 26*d* that is formed integral with said top and to be in engagement with the annular detent 24*g* which the cylindrical support 24*d* of base 24 does have. A short annular recess formed by cutting out the top end of outer periphery of the smaller-diameter portion 26*c* will serve to provide an annular clearance for receiving the O-ring 28, when the cylindrical support 24*d* is fitted on the inner cylinder 26*i*.

The rubber stopper 27 is fitted in the lower larger-diameter portion 26*e* of said inner cylinder 26*i*.

In natural state of the rubber stopper 27 not yet press-fitted in the cap 26, it assumes a diameter slightly larger than the larger-diameter portion 26*e* of said inner cylinder 26*i* which this cap comprises. With this stopper having been pressed in the said portion 26*e*, the outer periphery of stopper 27 will stand in a forced contact with the inner periphery of larger-diameter portion 26*e*, to thereby keep airtight the interior of said inner cylinder 26*i*. A central round recess formed in this stopper 27 will facilitate the pricking of a communication needle mentioned above.

Now, a process for assembling the infusion vessel 20 of this embodiment will be exemplified, with the vessel being charged with given proper amounts of a liquid medium and a selected medicine.

At first, the flange 11*d* of vessel body 11 will be fusion bonded to the flange 25*f* of cylindrical medicine chamber 25. Then, the given amount of the medium of an infusion liquid will be poured through this holder and into the space 11*a* of vessel body 11. The infusion medium may be the same as or similar to that in the first embodiment.

Subsequently, the end rod 24*a* of base 24 will be fitted in the central bore 23*a* of the first mentioned stopper 23, and the O-ring 28 will be fitted on the outer periphery of smaller-diameter portion 26*c* which the inner cylinder 26*i* of cap 26 comprises. Then, the top of this inner cylinder 26*i* is fitted in the annular recess 24*f* that is formed in the cylindrical support 24*d* of base 24, so that the annular lug 26*d* engages with annular detent 24*g* so as to be latched thereby.

In this state, the handling cap 26 is firmly secured to the base 24 on which the stopper 23 is mounted. However, since the engagement of annular lug 26*d* with annular detent 24*g* merely inhibits the latter from making an axial displacement relative to the former, such a base 24 can naturally spin relative to the cap 26.

At the next step, the handling cap 26 having been rendered integral with the stopper 23 and base 24 will be guided by said stopper into the cylindrical medicine chamber 25 so as to engage therewith. In detail, the lugs 26*b* of cap body 26*a* are forced to advance in and along the respective vertical groove 25*g* formed in said cylindrical holder 25. As a result, each lug 26*b* will ride over a protrusion 25*e* and consequently enter the corresponding helical slide groove 25*d*.

The handling cap 26 thus brought into an complete engagement with the cylindrical holder 25 will set the stopper 23 at its position where it is pressed against the sealing portion 25*b* of said holder, thereby rendering liquid-tight the infusion medium space 11*a*. Further, the O-ring 28 in this state ensures a liquid-tight relationship between the outer periphery of inner cylinder 26*i* of cap 26 and the inner periphery of larger-diameter portion 25*c* of said cylindrical holder 25.

Subsequent to the steps described above, a given amount of medicine that is solid (powdery) or liquid will be supplied through the cap's opening 26*g*. The medicine will thus enter the medicine chamber 25*a*, through the communication holes 24*e* formed in the base's cylindrical support 24*d*, so as to be isolated in said holder 25*a*. Finally, the rubber stopper will be fitted tightly in the opening 26*g* to complete the assembly of the infusion vessel 20.

In this infusion vessel 20 thus assembled, the first mentioned stopper 23 keeps liquid-tight the medium space 11*a*, and this stopper 23 co-operates with the O-ring 28 and the rubber stopper 27 to maintain airtight-ness of the medicine chamber 25*a*.

The infusion vessel 20 kept in such a state in this embodiment will then be put into storage or transported.

An operation for establishing liquid communication between the space and holder, as well as subsequent flow of the infusion liquid in response to displacement of the stopper 23, will now be described.

In order to start instillation, the handling cap 26 for the vessel 20 must be driven to circumrotate anti-clockwise (when seen upwards in FIG. 5(*c*) of the drawings). Because the slide grooves 25*d* in the stationary and cylindrical medicine chamber 25 are in engagement with the lugs 26*b* of cap 26, this cap will be urged downwards while rotating anti-clockwise about said holder. With such lugs 26*b* subsequently riding over the respective lugs 25*h* in the grooves 25*d* so as to be held thereby immovable any longer, such an initial operation to turn the cap 26 finishes.

Figure 6A:
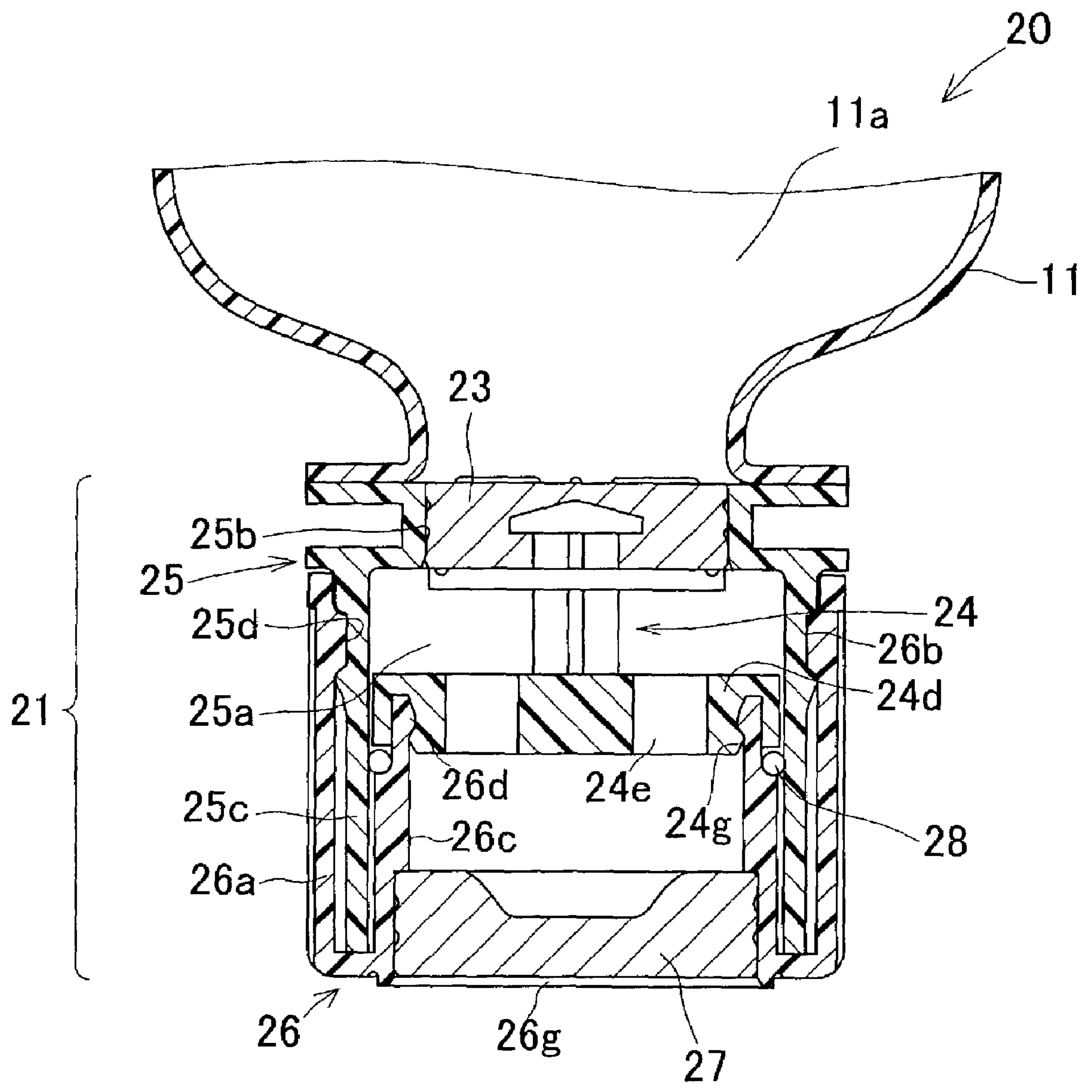
FIG. 6(*a*) is a vertical cross section of the infusion vessel shown in FIGS. 4(*a*) and 4(*b*), wherein its medicine chamber is not in communication with its medicine chamber.
Figure 6B:
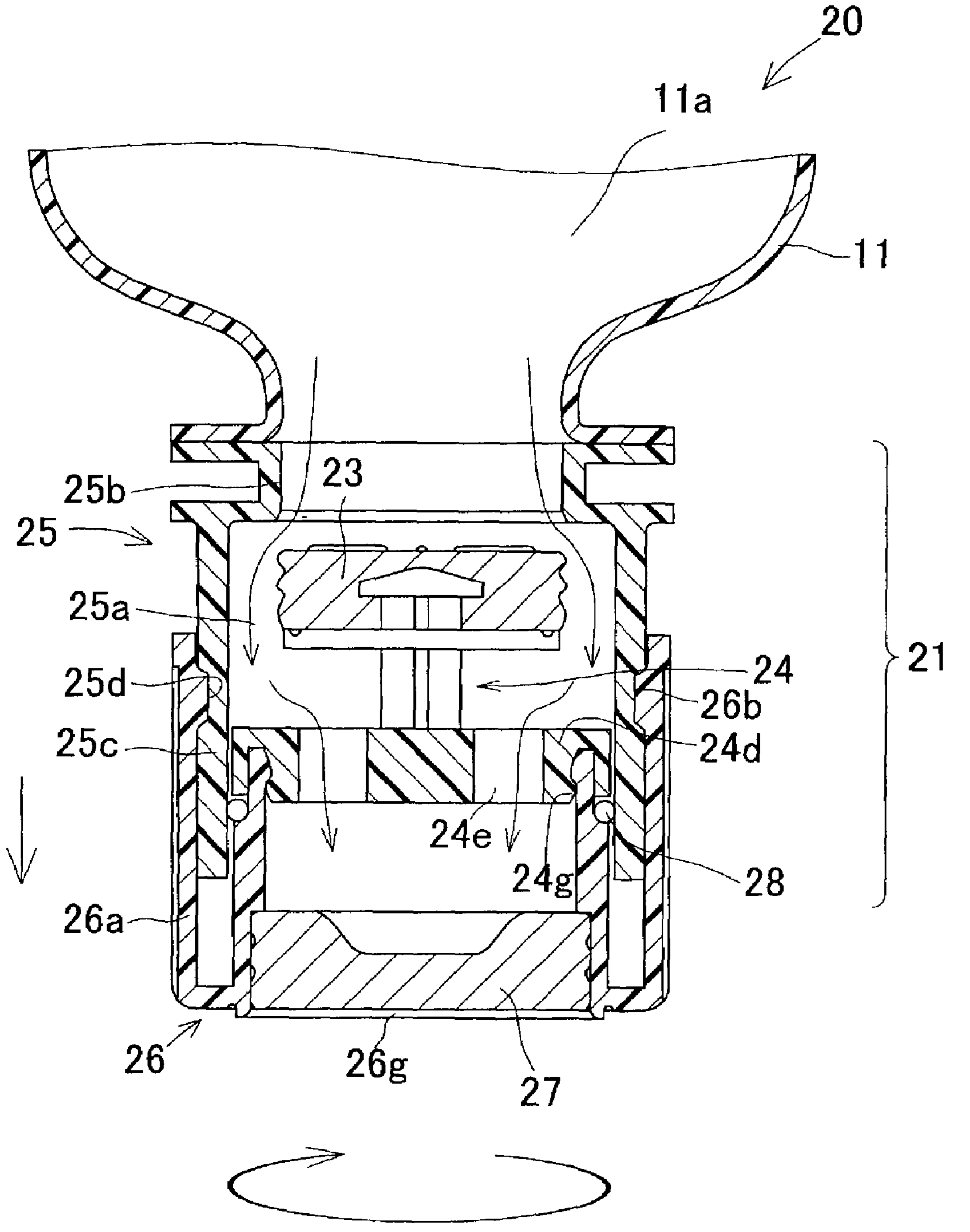

FIG. 6(*b*) shows that as the stopper 23 removes away from the sealing portion 25*b* of medicine chamber 25, there will appear communication passages allowing the infusion medium or liquid to flow down from the space 11*a* into the cylindrical medicine chamber 25*a*.

The O-ring 28 functions to keep airtight the medicine holder 25 holding therein the medicine against the handling cap 26 (its inner cylinder 26*i*), although such a rotation thereof.

Once such a communication is established, the vessel 20 will be subjected to vibration so as to intermix (dissolve or disperse) the medicine with the infusion medium. A communication needle (not shown) will then be thrust through the rubber stopper 27, so as to start instillation.

Thus, both the medicine chamber 25*a* and medium space 11*a* are kept airtight and liquid-tight, protecting them from foreign matters or various bacteria. Such an effect is not affected adversely, whether communication has not yet been established, or is just being or has already been established in the infusion vessel 20 of the present embodiment. Simple rotation of the handling cap 26 will now suffice well to blend the medicine with the infusion medium, thereby simplifying works required to perform an infusion treatment.

Although the inner cylinder of handling cap 26 in this embodiment is in engagement with the cylindrical support 24*d* of base 24 so as to move relative thereto only in axial direction, the invention is not delimited to such a configuration of the relevant members. Instead, it may be of any other shape such that those lugs 26*d* and 24*g* are replaced with certain grooves in the support 24*d* and protrusions in the inner cylinder 26*i*. In this case, due to the protrusions engaging these grooves, the support will be able to spin while making an axial displacement. Rotation of the handling cap 26 will then cause the stopper 23 to move axially and downwards, while spinning about its axis.

The process exemplified above to assembly the infusion vessel 20 is not intended to delimit the scope of invention. Although the fusion bonding of the medicine holder 25 for holding medicine to the vessel body 11 is carried out at first in the described example, this step may alternatively be conducted as a final step. In this case, the cap 26 having the base 24 integral with stopper 23 incorporated therein will be fitted in the medicine holder 25 at first. The medicine chamber 25*a* will subsequently be filled with the medicine and closed with the rubber stopper 27, so that the discharge mouth 21 is previously prepared in its complete state. Such a finished discharge mouth 21 will finally be fusion-bonded to the vessel body 11.

Figure 7A:
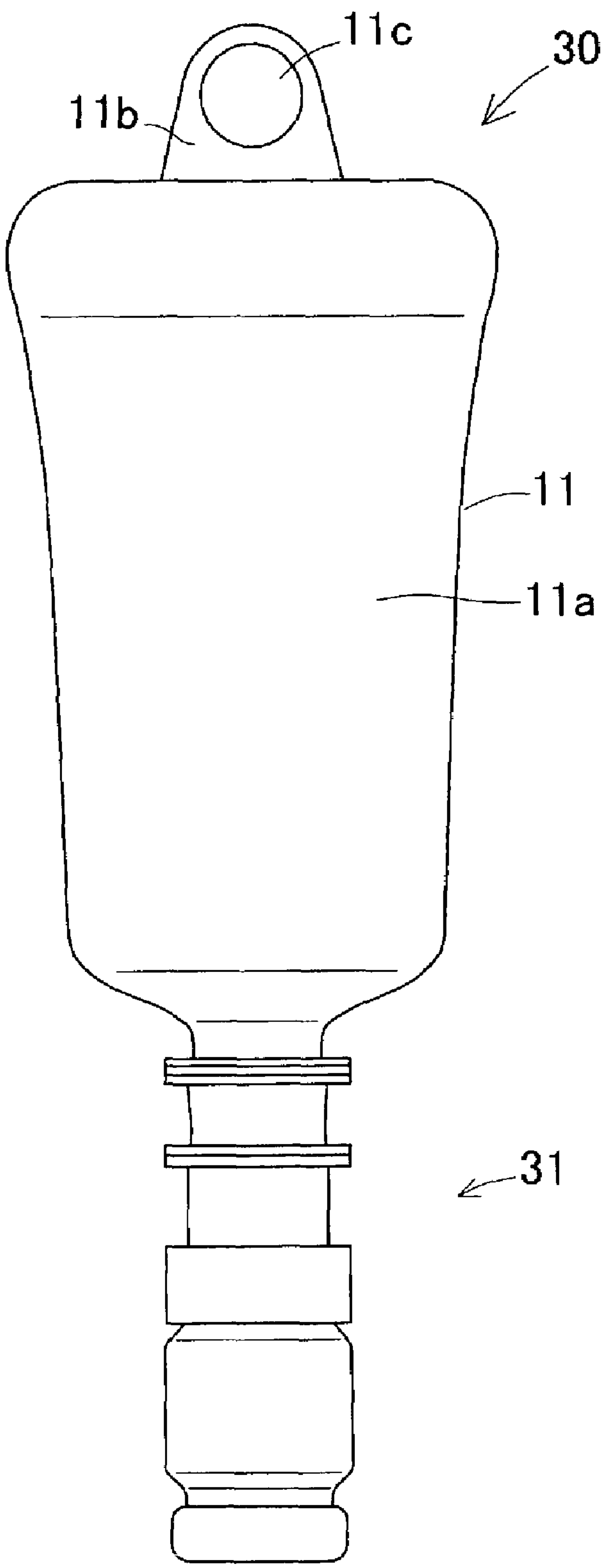
FIG. 7(*a*) is a front elevation of an infusion vessel provided in a third embodiment.
Figure 7B:
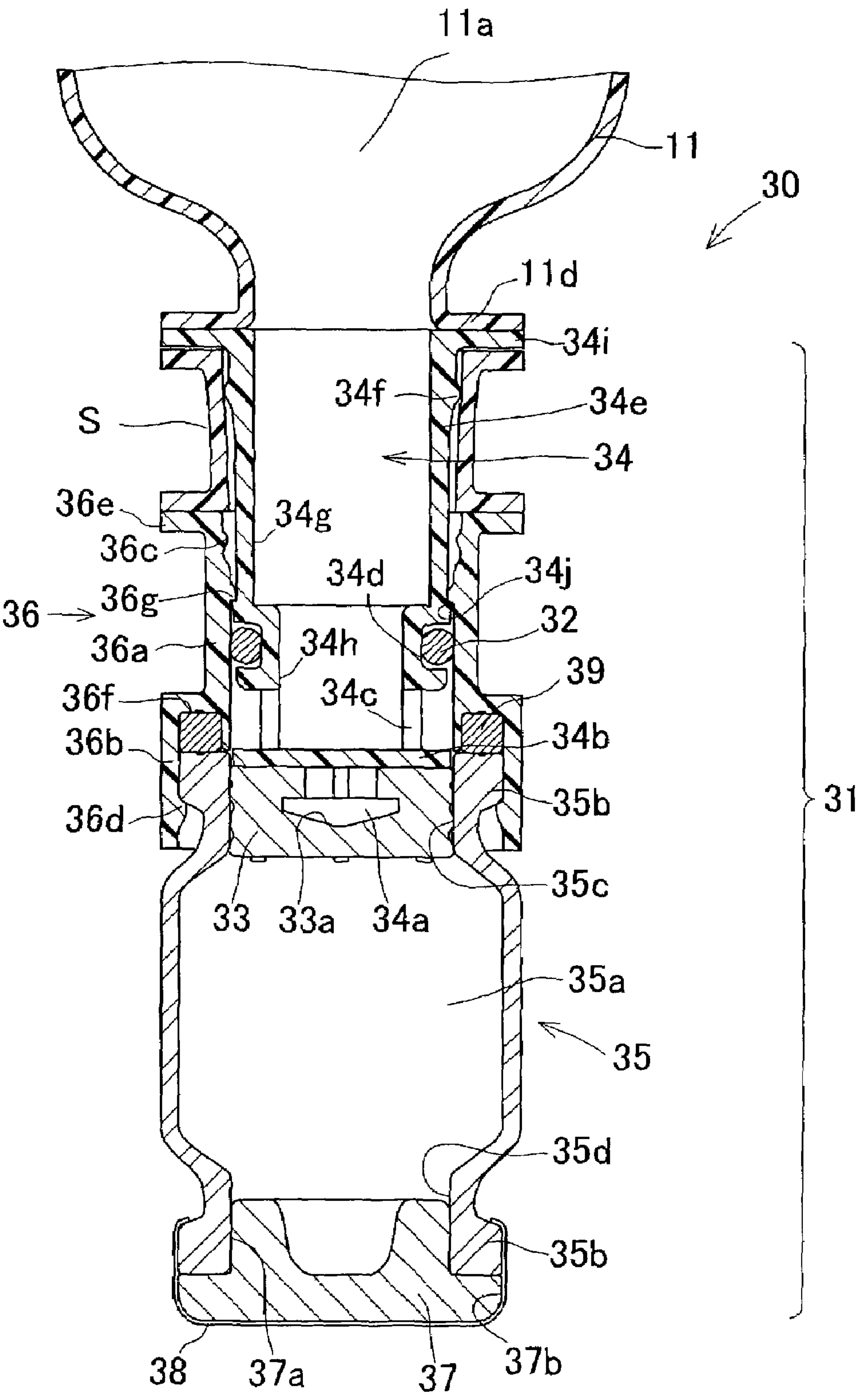

FIGS. 7(*a*) to 8(*b*) show an infusion vessel 30 that is provided in a third embodiment of the present invention (as set forth particularly in the accompanying claims 8 and 9). Also, the infusion vessel 30 comprises a vessel body 11 similar to those in the first and second embodiments, and a cylindrical discharge mouth 31 continues down from the lower end of this vessel body 11.

As seen in FIG. 7(*b*), this discharge mouth 31 comprises a stopper (separator) 33, a base 34 mainly composed of a support cylinder, and a medicine holder 35 with a cavity serving as a medicine chamber 35*a*. The discharge mouth 31 further comprises a connector 36 fixedly fitting on one end of the medicine holder 35 so as to move axially of the base 34. This discharge mouth 31 still further comprises a rubber stopper 37 fitted in the other end of said medicine holder 35, and an aluminum seal 38 for covering and protecting the rubber stopper 37. The said mouth 31 yet still further comprises an O-ring 38, a packing 39, and a spacer 'S' for inhibiting the connector 36 from making any unintentional displacement.

The first mentioned stopper 33 is a generally columnar gasket of a butyl rubber, and has a central bore 33*a* with a closed bottom and shaped to fit on a portion of the base 34.

This base 34 is composed of an end rod 34*a* for engagement with the bore 33*a* of stopper 33, a flange 34*b* contacting the upper surface of stopper 33, an intermediate rod 24*c* depending down from flange 24*b*, and a cylindrical support 34*e* continuing upwards from flange 34*b*. Such a base 34 may for example be formed by injection of a high-density polyethylene or the like resin.

The cylindrical support 34*e* is composed of an upper larger-diameter portion 34*g* and a lower smaller-diameter portion 34*h*. An upper edge of the cylindrical support 34*e* (larger-diameter portion 34*g*) is bent radially outwards to form a flange 34*i*. An annular lug 34*f* is formed integral with the outer periphery of a region adjacent to the said upper edge of said cylindrical support 34*e*.

An annular recess 34*d* for receiving therein the O-ring 32 is formed in the outer periphery of an upper region of the said smaller-diameter portion 34*h*. A plurality of communication apertures 34*c* are formed in a lower region of this portion 34*h*.

An annular detent 34*j* is formed in the outer upper periphery of said portion 34*h* and above the annular recess 34*d*.

The medicine holder 35 for storing therein a medicine is a generally cylindrical bottle or a similar article made of a proper hard resin. A sealing portion 35*c* of this part 35 is formed as an upper region for temporarily and liquid-tightly surrounding and contacting the stopper 33. This medicine holder 35 expands itself towards its lower region so as to be of a constant at its middle height region, before reducing again its diameter near its lower end where an opening 35*d* is formed to be press-fitted on the rubber stopper 37. Thus, the cylindrical medicine chamber 35 is composed such an upper and lower regions shaped symmetrical with each other about its center.

Both the upper and lower rims of this medicine holder 35 protrude radially outwards to provide annular protuberances 35*b*.

Under a natural condition of the sealing portion 35*c* not yet fitted on the stopper 33, it has been of a diameter slightly larger than the diameter of this stopper. Thus, a liquid-tight sealing will be ensured between the said portion 35*c* and said stopper 33 fitted therein.

The connector 36 that is composed of a smaller-diameter portion 36*a* and a larger-diameter portion 36*b* is a generally medicine holder made of a polypropylene or the like thermoplastic resin. The end of the smaller-diameter portion 36*a* is bent to provide a flange 36*e*, and an annular lug 36*c* is formed integral with the inner periphery of this portion 36*a* and adjacent to this flange 36*e* so as to engage with the annular lug 34*f* of cylindrical support 34. At a middle height of the inner periphery of smaller-diameter portion 36, an annular latch 36*g* is formed to engage with the annular detent 34*j* of cylindrical support 34*e* of the base 34.

A further annular latch 36*d* is formed as the inner peripheral end region of said larger-diameter portion 36*b* of connector, such that the annular protuberances 35*b* of medicine chamber 35 is kept in engagement with this further latch 36*d*.

The rubber stopper 37 also is composed of a smaller-diameter portion 37*a* and a larger-diameter portion 37*b*. Outer diameter of the smaller-diameter portion 37*a* is slightly larger than inner diameter of the opening 35*d* of said cylindrical medicine chamber 35. The larger-diameter portion 37*b* is generally of the same outer diameter as the lower end of this medicine chamber 35. With the smaller-diameter portion 37*a* being press-fitted in the said opening 35*d* of holder 35, an airtight sealing thereof will be ensured.

The O-ring 32 is a sealing member of a round cross section to be fitted in the annular recess 34*d* of base 34. On the other hand, the packing 39 is of a generally square in cross section to be interposed between the top surface of the cylindrical medicine chamber 35 and a shoulder 36*f* of the connector facing said surface.

The spacer 'S' is made of a polypropylene or the like thermoplastic resin, and is C-shaped in cross section as if an axial zone were cut off a collar. A top and bottom ends of this spacer 'S' are bent outwards to give integral flanges.

Such a spacer 'S' fits on the outer periphery of cylindrical support 34*e* which the base 34 comprises.

Now, a process for assembling the infusion vessel 30 of this embodiment will be exemplified, with the vessel being charged with given proper amounts of a liquid medium and a selected medicine.

At first, the end rod 34*a* of base 34 will be fitted in the central bore 33*a* of stopper 33, with the O-ring 32 being forced into the annular recess 34*d* which the base 34 comprises.

On the other hand, the packing 39 will be incorporated into the connector 36 so as to bear against its shoulder 36*f*. Subsequently, the end of cylindrical medicine chamber 35 will be urged into the larger-diameter portion 36*b* of this connector, until the upper annular protuberance 35*b* will be hooked in place by the annular latch 36*d*. In this way, the connector 36 is consolidated with the cylindrical medicine chamber 35 in such a state that the packing 39 brought into close contact with both the shoulder 36*f* and the top face of this holder 35.

Subsequent to such preparative procedures, the base 34 having the stopper 33 attached thereto will be pressed into the smaller-diameter portion 36*a* of connector 36, with the stopper 33 then leading the base. The annular detent 34*j* is thus brought into a fixed engagement with the annular latch 36*g*.

In this state of members, the stopper 33 stands liquid-tightly in the sealing portion 35*c* of cylindrical medicine chamber 35, and the O-ring 32 thereby renders airtight the cylindrical support 34*e* of base 34 within and relative to the connector 36.

A proper amount of an infusion medium will then be supplied to the space 11*a* of vessel body 11, before fusion-bonding its flange 11*d* to the base's flange 34*i* air-tightly. The kind of such an infusion medium is identical with or similar to that used in the first embodiment. Thereafter, the spacer 'S' will be forced to fit on the outer periphery of the base's cylindrical support 34*e*.

A given quantity of desired medicine will thus be introduced into the medicine chamber 35*a* of medicine holder 35, and the rubber stopper, wherein the sort of this medicine is identical with or similar to that used in the first embodiment. Finally, aluminum seal 38 will be stuck to the rubber stopper 37 so as to tightly cover its outer surface and the end of cylindrical medicine chamber 35.

In this infusion vessel 30 thus assembled, the first mentioned stopper 33 and the rubber stopper 37 keep liquid-tight the medicine chamber 35*a*, and this stopper 33 cooperates with the O-ring 32 and packing 39 to keep liquid-tight the medium space 11*a*.

The infusion vessel 30 kept in such a state in this embodiment will then be put into storage or transported.

An operation for establishing liquid communication between the space and holder so as to enable subsequent flow of the infusion liquid is as follows.

The spacer 'S' has to be removed at first from the base 34, so that the cylindrical medicine chamber 35 can subsequently be thrust towards the base 34 (cylindrical support 34*e*). The connector annular lug 36*c* thus engaged with the cylindrical support annular lug 34*f* will retain this connector 36 fixedly and fully overlaid on this support 34.

Figure 8A:
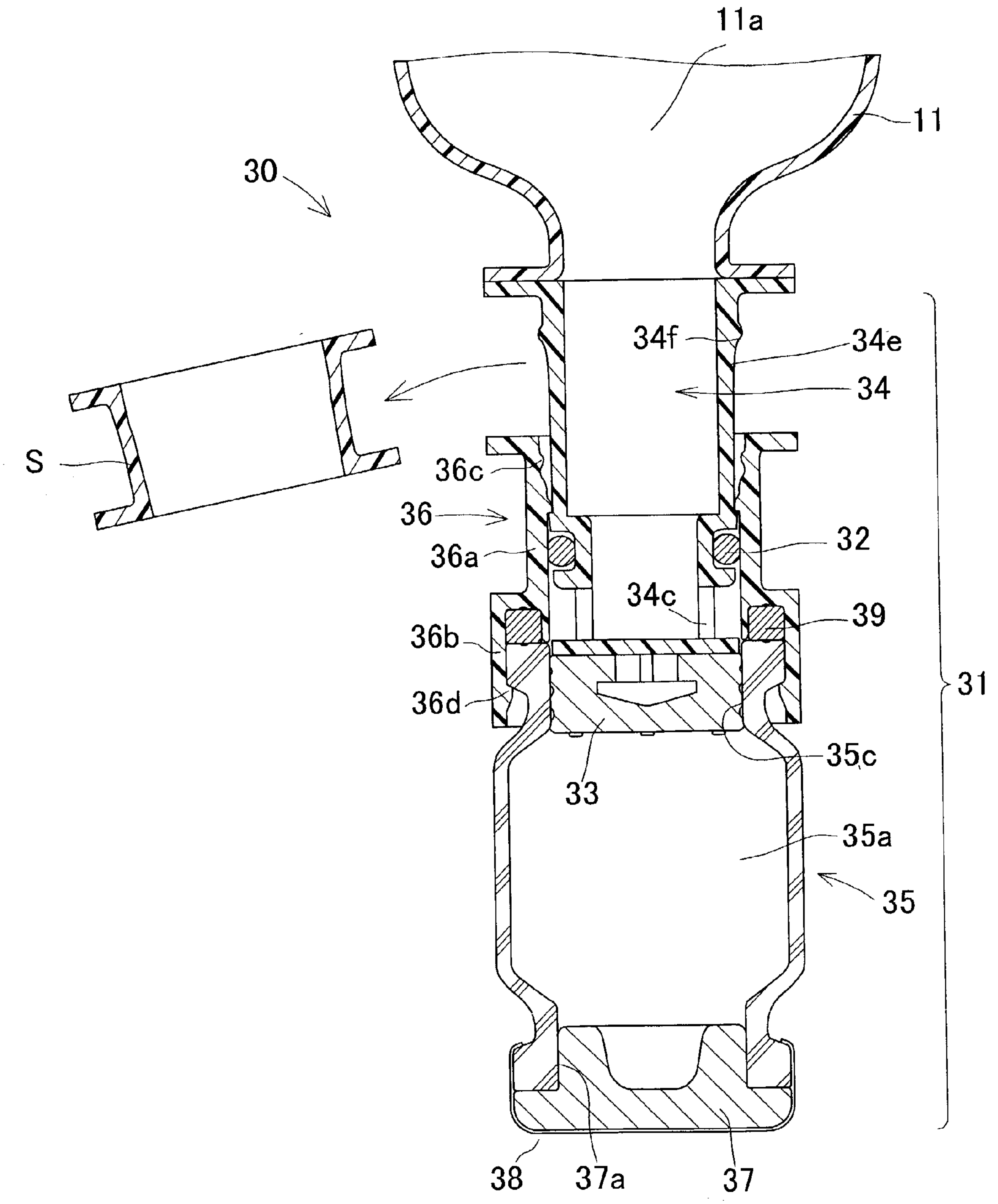
FIG. 8(*a*) is a vertical cross section of the infusion vessel shown in FIGS. 7(*a*) and 7(*b*), wherein its medicine chamber is not in communication with its medicine chamber.
Figure 8B:
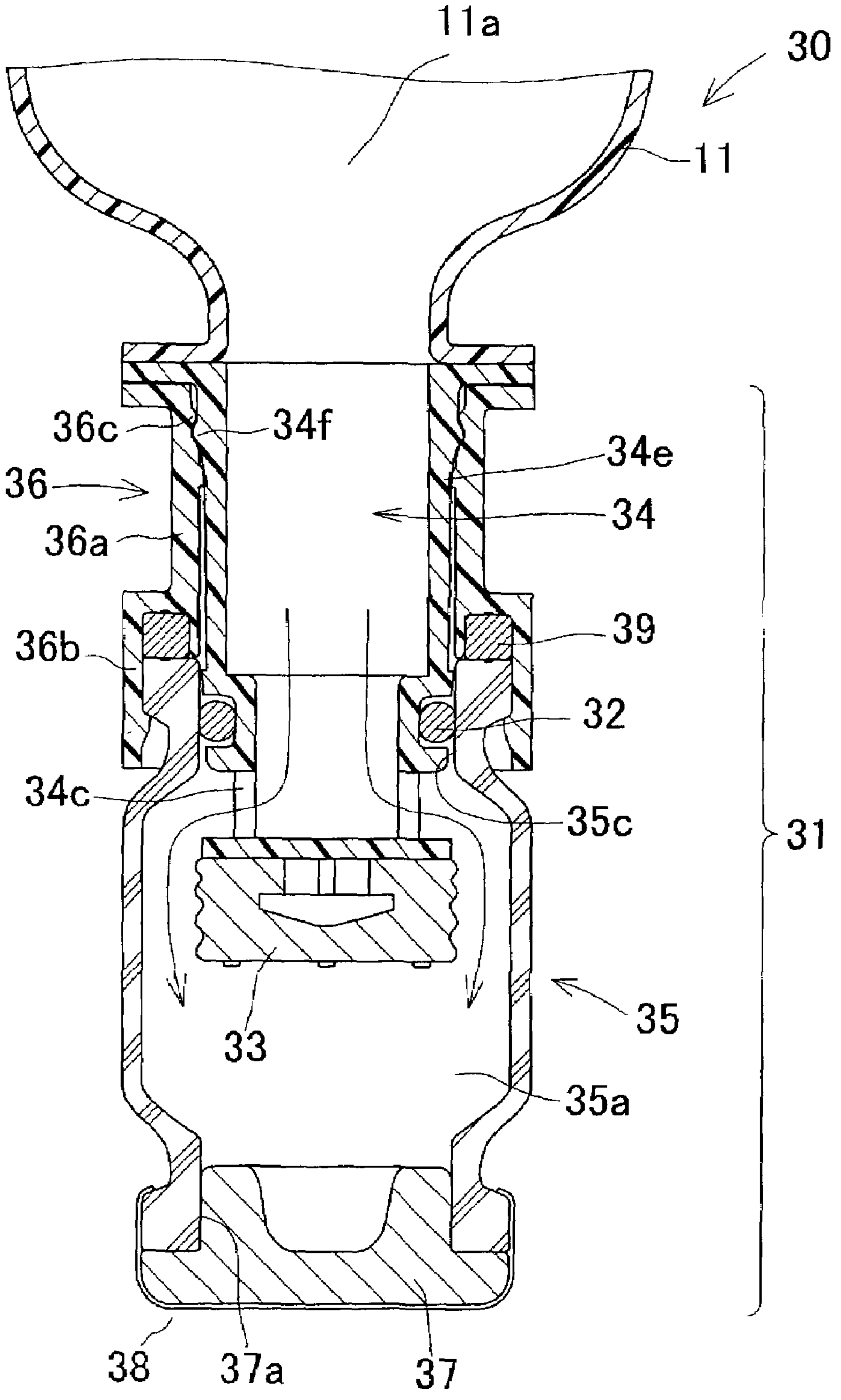

As a result, as seen best in FIG. 8(*b*), the stopper 33, the stopper 33 is displaced off the sealing portion 35*c* and into the larger-diameter section of cylindrical medicine chamber 35. In this state, the cylindrical support 34*e* and apertures 34*c* of the base 34 do serve to establish a liquid communication between the space 11*a* and cylindrical medicine chamber 35*a*, allowing the infusion medium to flow from the former 11*a* into the latter 35*a*.

The O-ring 32 in this embodiment will keep an airtightness between the base 34, connector 36 and cylindrical medicine chamber 35, during and after the inward thrusting of this holder 35.

After establishing communication in this manner, the vessel 30 will be vibrated to intermix (dissolve or disperse) the medicine with the infusion medium. The aluminum seal 38 will then be removed so that a communication needle (not shown) may penetrate the rubber stopper 37, so as to start instillation.

Thus, both the medicine chamber 35*a* and medium space 11*a* are kept airtight and liquid-tight, protecting them from foreign matters or various bacteria. Such an effect is not affected adversely, whether communication has not yet been established, or is just being or has already been established in the infusion vessel 30 of the present embodiment.

Simple removal of the spacer 'S' and easy inward thrust of the medicine cylinder 35 will render this injection vessel ready to blend the medicine with the infusion medium, thereby simplifying works required to perform infusion treatment.

Although the connector 36 is exemplified as a discrete member fitting on the medicine cylinder 35 in this embodiment, these connector 36 and cylinder 35 may alternatively be prepared as an integral part.

Further, the process exemplified above to assembly the infusion vessel 30 is not intended to delimit the scope of invention.

Figure 9A:
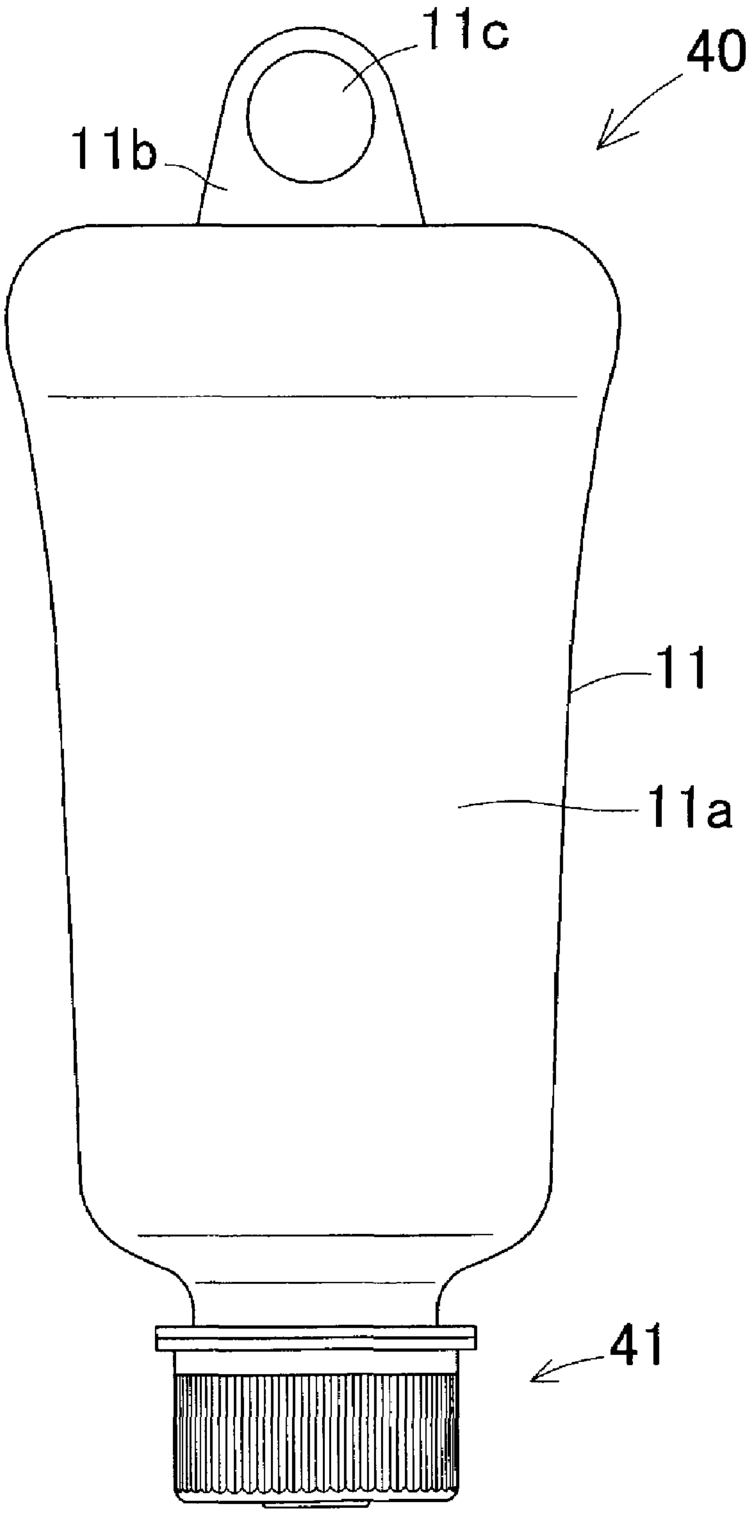
FIG. 9(*a*) is a front elevation of an infusion vessel provided in a fourth embodiment.
Figure 9B:
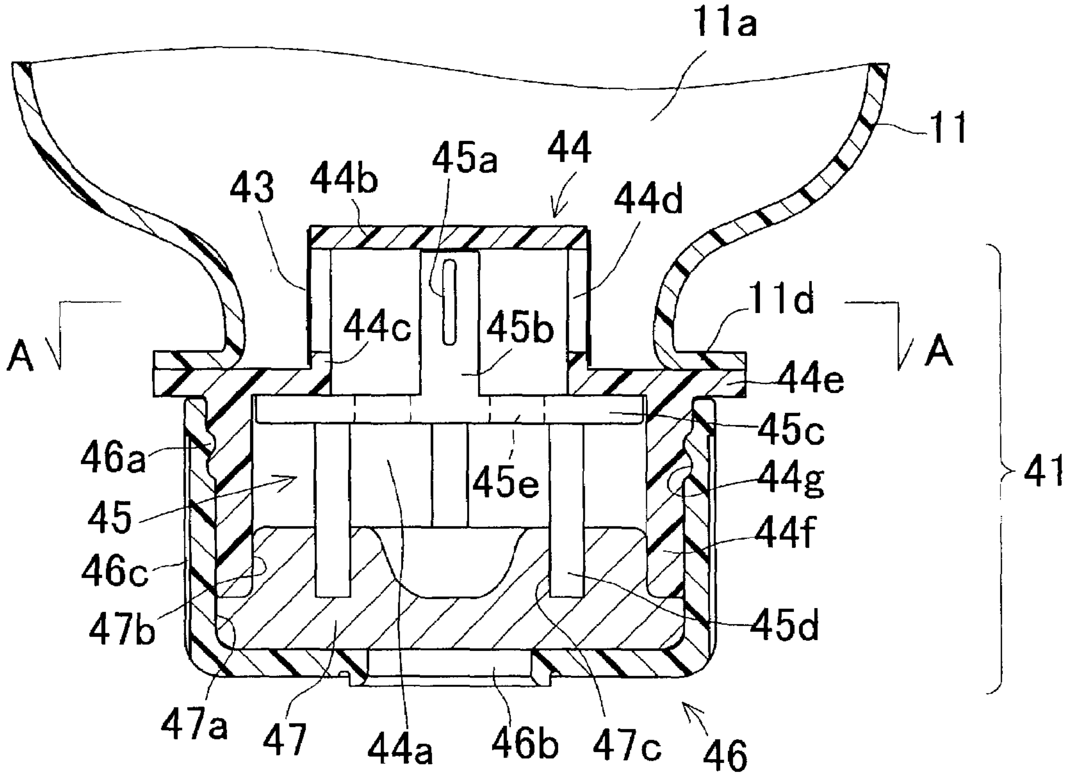
Figure 9C:
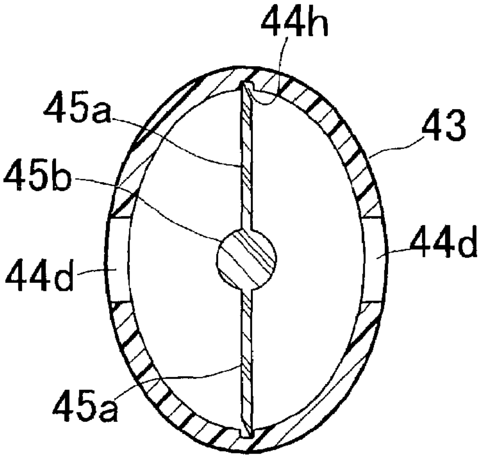

FIGS. 9(*a*) to 11(*c*) show an infusion vessel 40 that is provided in a fourth embodiment of the present invention (as set forth particularly in the accompanying claims 10 and 11). Also, the infusion vessel 30 comprises a vessel body 11 similar to those in the first and second embodiments, and a cylindrical discharge mouth 41 continues down from the lower end of this vessel body 11.

As seen in FIG. 9(*b*), the discharge mouth 41 comprises a sealing stopper (separator) 43 made of a thin film, and a medicine holding cylinder 44 that is covered with the stopper 43 so as to define therein a cavity serving as a medicine chamber 44*a*. The discharge mouth 31 further comprises a releaser 45 for deforming the sealing stopper 43 to break a tight closure of the medicine chamber 44*a*. This discharge mouth 41 in this infusion vessel still further comprises a handling cap 46 fitted on and rotating around the medicine holding cylinder 44, and a rubber stopper 47 press-fitted in the handling cap 46.

The thin film as the sealing stopper 43 that may be a short tube formed of a polypropylene or the like thermoplastic resin is bonded to the outer periphery of medicine holding cylinder 44, using an adhesive resin.

The medicine holding cylinder 44, also formed of the same or a different polypropylene or the like thermoplastic resin, is a complex cylinder. This complex cylinder is composed of a partitioning portion 44*c* elliptic in cross section and a larger-diameter portion 44*f* of a round cross section.

The partitioning portion 44*c* having a closed top 44*b* does comprise two square communication aperture 44*d*, that are formed respectively in and through peripheral wall zones facing one another in the horizontal direction including minor axis of said elliptic cross section. Two vertical grooves 44*h* are formed in other inner peripheral zones that face one another across the vertical axis of this portion 44*c*, in the other horizontal plane including major axis.

The larger-diameter portion 44*f* is a cylindrical portion formed coaxially integral with partitioning portion 44*c*, and a flange 44*e* protrude outwards radially from the boundary between these portions 44*f* and 44*c*. An annular detent 44*g* is formed integral with and around the outer peripheral surface of larger-diameter portion 44*f*. The sealing stopper 43 bonded with the adhesive resin to the outer periphery of partitioning portion 44*c* does function to re-openably close the communication apertures 44*d* at their outer openings.

Thus, such a partitioning portion 44*c* cooperates with sealing stopper (thin film) 43 to serve as a separator in this embodiment.

The releaser 45 mentioned above comprises a disc-like base 45*c*, an upper rod 45*b* erected from the center of base 45*c*, two vanes 45*a* protruding sideways from an upper region of the rod 45*b*, and four lower rods 45*d* depending from the base 45*c*. This releaser 45 may be an article made by injection molding a high-density polyethylene or the like plastics.

The base 45*c* of releaser 45 has an outer diameter slightly smaller than the inner diameter of larger-diameter portion 44*f* so that the releaser 45 can spin within this portion. Horizontal communication apertures 45*e* formed in and through the releaser base 45*c* are arranged radially.

Each of the thin and elastic vanes 45*a* extending out from the rod 45*b* is of a horizontal length slightly larger than the major radius of elliptic partitioning portion 44*c*. Distal ends of such vanes 45*a* are normally and respectively engaged with the vertical grooves 44*h*. It is however to be noted that the normal horizontal length of each vane 45*a* is significantly larger than the minor radius of elliptic partitioning portion 44*c*.

A round recess (not shown) is formed in the top of upper rod 45*b* so as to rotatably receive a round lug (not shown) that protrudes down from the elliptic top of 44*b* of medicine holding cylinder 44.

Figure 10A:
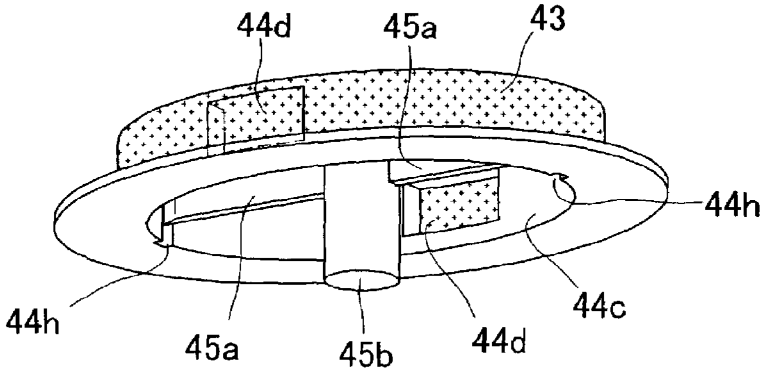
FIGS. 10(*a*), 10(*b*) and 10(*c*) are perspective views of the infusion vessel shown in FIGS. 9(*a*) to 9(*c*), wherein a process of bringing its medicine chamber into a fluid communication with its medium space is illustrated.
Figure 10B:
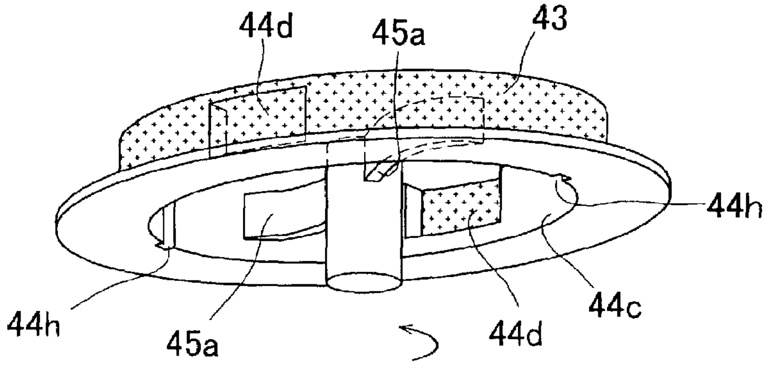
Figure 10C:
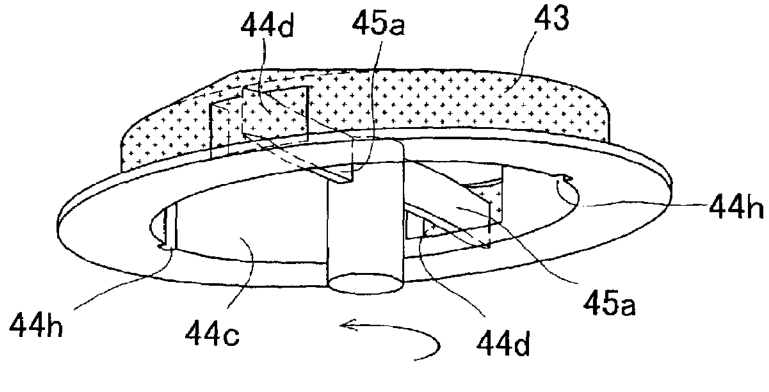
Figure 11A:
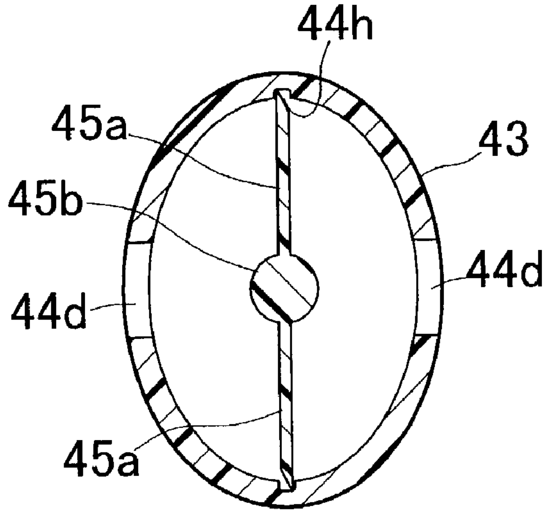
FIGS. 11(*a*), 11(*b*) and 11(*c*) are overall vertical cross sections of discharge mouth of the infusion vessel shown in FIGS. 9(*a*) to 9(*c*), wherein the process of bringing its medicine chamber into a fluid communication with its medium space is illustrated.
Figure 11A:
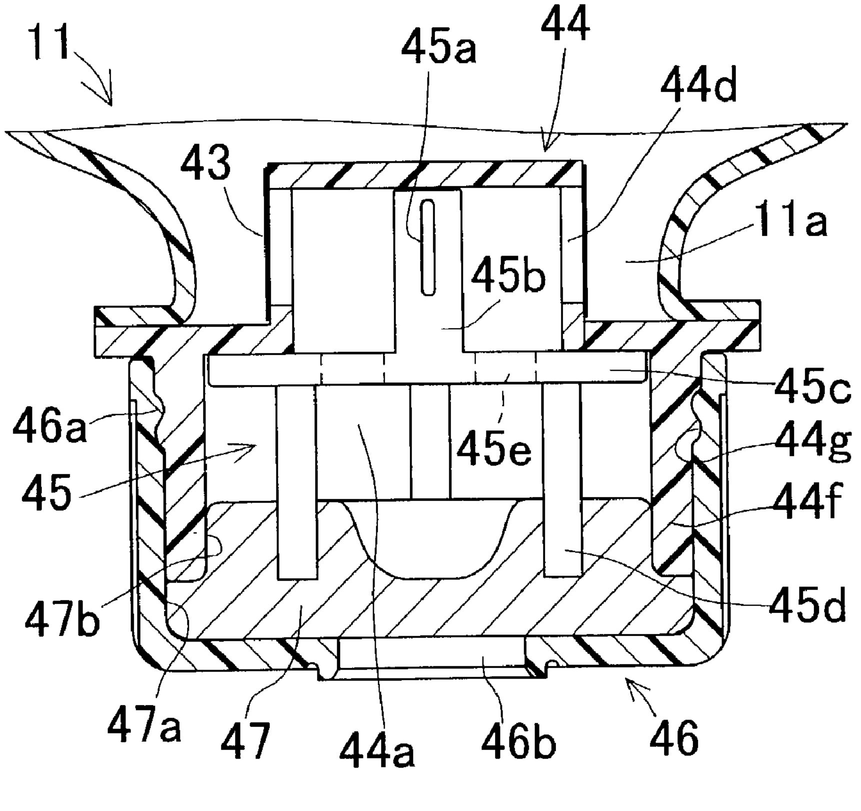
Figure 11B:
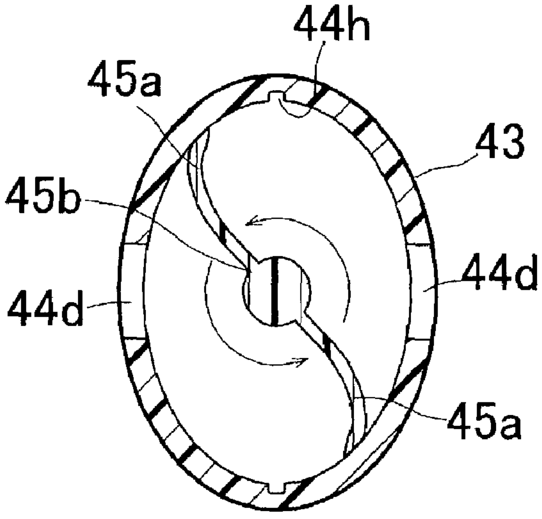
Figure 11B:
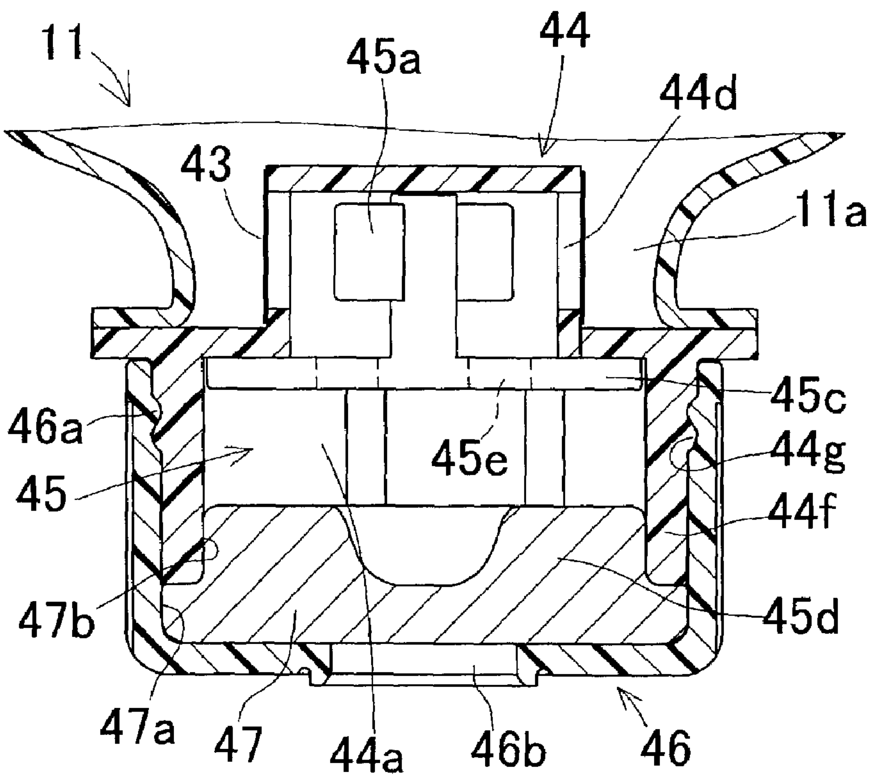
Figure 11C:
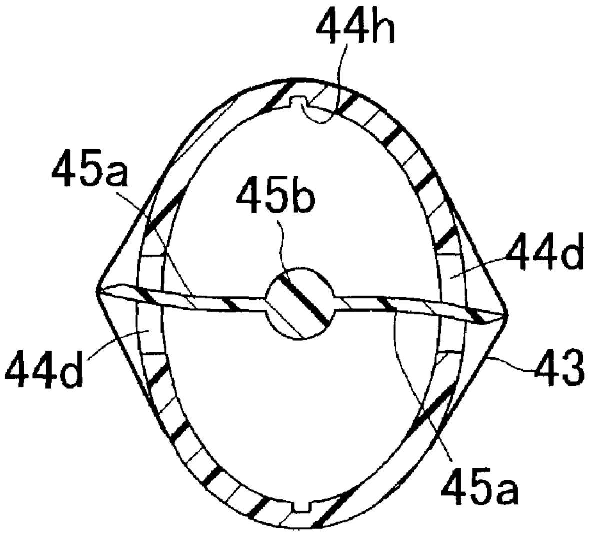
Figure 11C:
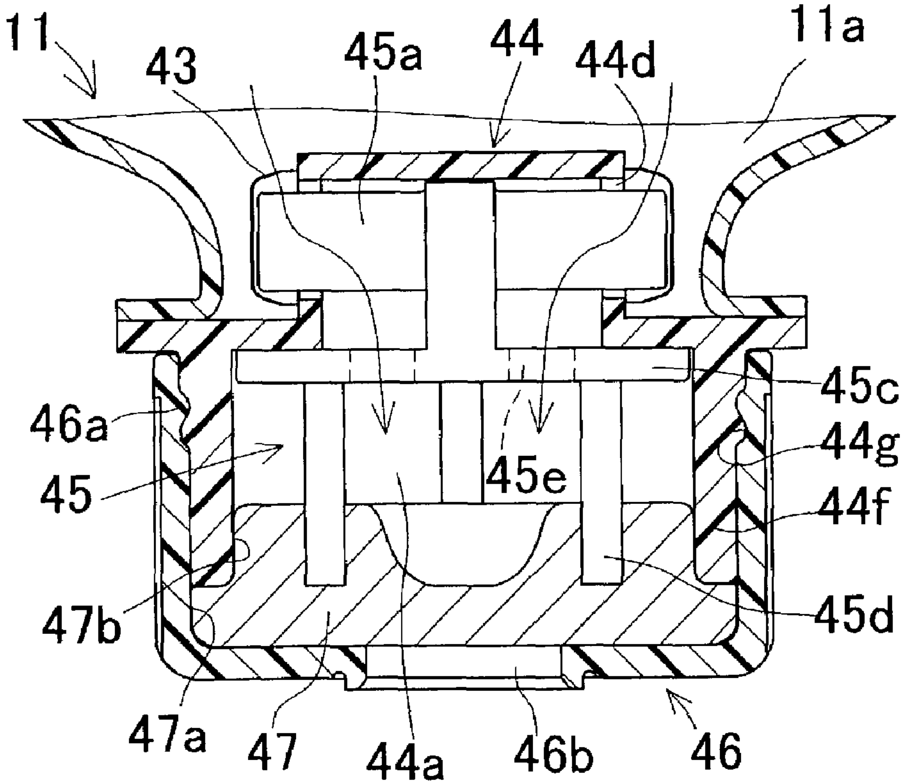

The releaser 45 incorporated in this cylinder 44 can rotate within the partitioning portion 44*c* thereof, in such a manner that their vanes 45*a* disengage from the vertical grooves 44*h* formed in said portion 44*c* as shown in FIGS. 10(*a*) to 10(*c*). They 45*a* will rotate together with the rod 45*b* and along the inner periphery of partitioning portion 44*c*, while being caused to make elastic deformation gradually and gently. As a result, the distal ends of them 45*a* will become in alignment with the apertures 44*d* so that they will elastically spring out of these apertures. Consequently, the regions of thin film (sealing stopper) 43 bonded to the outer periphery of partitioning portion 44*c* will be forced by such resilient recovery of those vanes 45*a* to expand outwards to bring the apertures 44*d* into their communicating state.

The handling cap 46 injection-molded of a polypropylene or the like thermoplastic resin is a cylindrical piece with a closed bottom and adapted to fit on the outer periphery of larger-diameter portion 44*f* which the medicine holding cylinder 44 comprises. A central portion of this cap 46 is opened to provide an aperture 46*b* enabling penetration of a communication needle (not shown) through this cap.

Annular protrusion 46*a* formed as a portion of the inner periphery of handling cap 46 is for engagement with the annular detent 44*g* *Anti-slip vertical indentations* 46*c* are engraved in the outer periphery of this handling cap 46.

The rubber stopper 47 press-fitted in the handling cap 46 is composed of a smaller-diameter portion 47*b* integral with a larger-diameter portion 47*a*. In natural state of this stopper 47 not yet press-fitted in the cap 26, its smaller-diameter portion 47*b* shows an outer diameter slightly larger than the inner diameter of larger-diameter portion 44*f* of medicine holding cylinder 44. Also in said natural state, the outer diameter of larger-diameter portion 47*a* of rubber stopper 47 is slightly larger than the inner diameter of handling cap 46. With this cap having the stopper 47 press-fitted therein and having been fitted itself on the cylinder 44, the lower end and an adjacent region of larger-diameter portion 44*f* will be kept airtight on the said rubber stopper 47.

Vertical cutouts 47*c* formed in the upper portion of rubber stopper 47 are for engagement with the vertical lower rods 45*d* of releaser 45. A central round recess formed in this stopper 47 will facilitate the pricking of a communication needle mentioned above.

Now, a process for assembling the infusion vessel 40 of this embodiment will be exemplified, with the vessel being charged with given proper amounts of a liquid medium and a selected medicine.

At first, an adhesive resin will be used to bond the sealing stopper (thin film) 43 to the outer periphery of partitioning portion 44*c* which the medicine holding cylinder 44 comprises. Thus, the communication aperture 44*d* of this cylinder 44 will be closed liquid-tightly.

On the other hand, a given amount of a selected infusion medium will be poured into space 11*a* of vessel body 11. The flange lid of this body is fusion-bonded to the flange 44*e* of medicine holding cylinder 44, thereby rendering airtight the space 11*a* against the interior of said cylinder. The kind of infusion medium is the same as or similar to that used in the first embodiment. In this manner, the medium space 11*a* is liquid-tightly closed with the sealing stopper 43.

Subsequently, the releaser 45 will be put in the medicine holding cylinder 44 so as to take such a position that the distal ends of its vanes 45*a* engages with vertical grooves 44*h* of the partitioning portion 44*c* of this cylinder 44. Thus, the round recess (not shown) in the top of upper rod 45*b* stands in engagement with the round lug (not shown) of the elliptic top of 44*b* of medicine holding cylinder 44.

After setting in place the members this way, a given amount of selected medicine that is the same as or similar to that used in first embodiment will be supplied to the medicine chamber 44*a*.

Then, the rubber stopper 47 will be positioned relative to the releaser 45 so that the former's cutouts 47*c* fit on the latter's rods 45*d*, respectively, with the former's smaller-diameter portion 47*b* fitting in the larger-diameter portion 44*f* of medicine holding cylinder 44. Finally, the handling cap 46 having the rubber stopper 47 fitted therein will be press-fitted on the medicine holding cylinder 44. In the infusion vessel 40 thus finished to have the annular protrusion 46*a* engaged with the annular detent 44*g*, the cap 46 cannot be displaced axially relative to this cylinder 44.

In this infusion vessel 40 thus assembled, the separator (the partitioning portion 44*c* and sealing stopper 43) keeps liquid-tight the infusion medium space 11*a*, and such a separator cooperates with the rubber stopper 47 to maintain liquid-tight the medicine chamber 44*a*.

The infusion vessel 40 kept in such a state in this embodiment will then be put into storage or transported.

An operation for establishing liquid communication between the space and holder, as well as subsequent flow of the infusion liquid, will now be described.

In order to start instillation, the handling cap 46 for the vessel 40 must be driven to circumrotate anti-clockwise (when seen upwards in FIG. 11(*b*) of the drawings). The releaser 45 will thus be driven to spin also anti-clockwise in unison with the cap 46, causing its vanes 45*a* to make elastic deformation so as to rotate along the inner periphery.

As shown in FIGS. 10(*c*) and 11(*c*), the distal ends of vanes 45*a* will reach the communication apertures 44*d* where they tend to elastically recover their natural position to jut out through these apertures. Consequently, regions of the thin film (stopper) 43 will be repelled off the partitioning portion 44*c* in order to open the communication apertures 44*d*.

With these apertures 44*d* being opened, the infusion medium will start to flow out of the space 11*a* into the medicine chamber 44*a*, though the other communication apertures 45*e* formed through the releaser 45.

The rubber stopper 47 in this vessel 40 will remain closely contacted with the lower end and the adjacent inner peripheral region of the larger-diameter portion 44*f* of medicine cylinder 44, to thereby keep them surely airtight.

After establishing communication in this manner, the vessel 40 will be vibrated to intermix (dissolve or disperse) the medicine with the infusion medium. A communication needle (not shown) guided through the handling cap's opening 46*b* may penetrate the rubber stopper 47, so as to start instillation.

The infusion vessel 40 of the present embodiment will never fail to keep airtight both the medicine chamber 44*a* and medium space 11*a*, protecting them from foreign matters or various bacteria. Simple rotation of the handling cap 16 suffices well to blend the medicine with the infusion medium, thereby simplifying works required to perform an infusion treatment and thus avoiding any error that have often resulted heretofore from intricate operations.

Although the separator in this embodiment is composed of the thin film bonded with a resin to the partitioning portion, the present invention is never delimited to such a particular structure. For example, a resin layer may be injected and laminated on a previously molded partitioning portion, or a tubular thermally shrinking film may be place to cover the communication apertures and then heated to permanently stick to the partitioning portion, in order to realize a liquid-tight closing of these apertures.

The process exemplified above to assembly the infusion vessel 40 is not intended to delimit the scope of invention.

Figure 12:
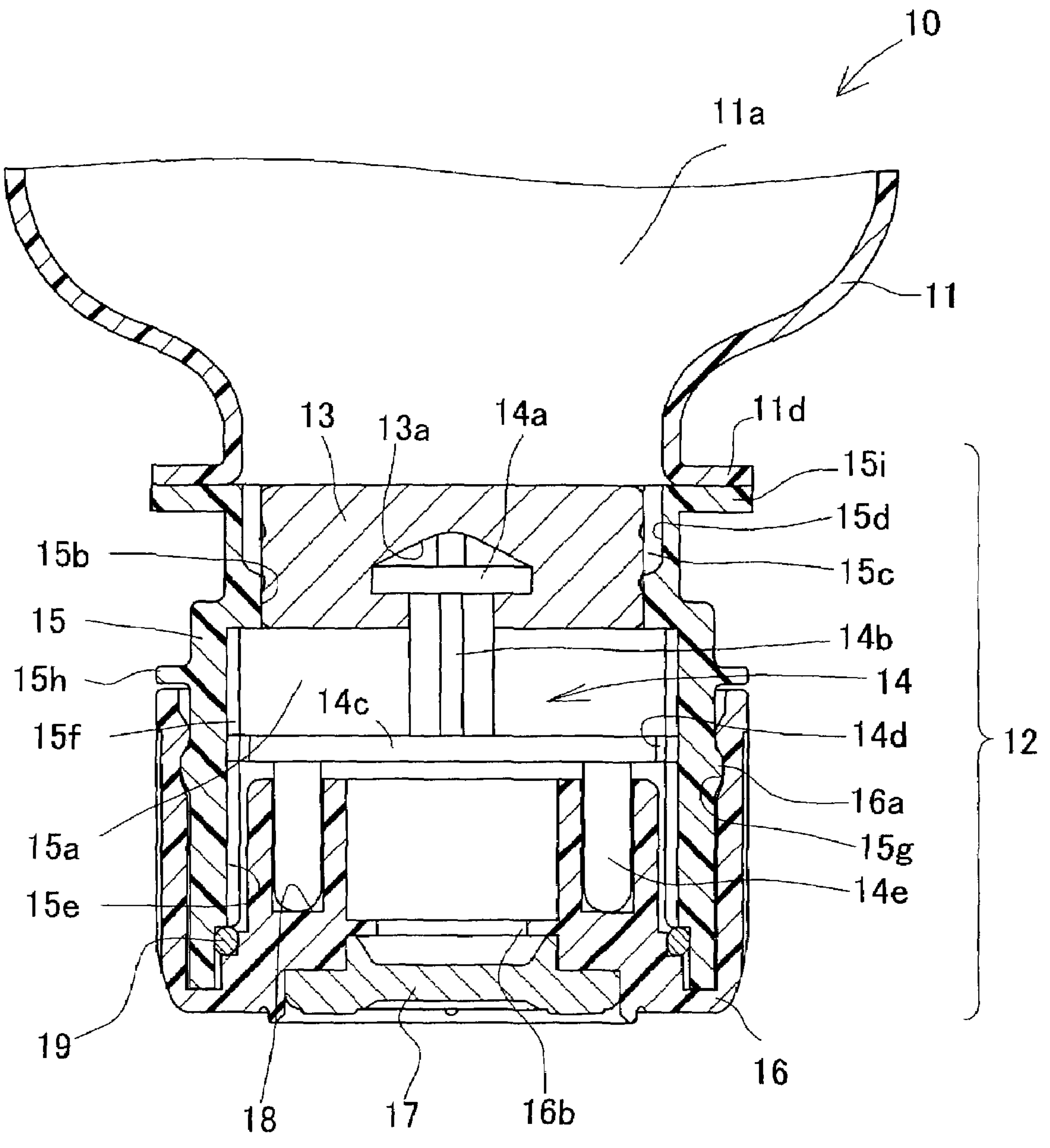
FIG. 12 is an enlarged cross section of a principal part of an infusion vessel provided in a fifth embodiment.

FIG. 12 shows an injection vessel 10 provided in a fifth embodiment of the invention (as set forth in the accompanying claim 5). Structural features, elements as well as functions and effects thereof that are the same as or similar to those in the first embodiment are not described here, but being merely indicated by the same reference numerals.

A cam mechanism employed herein to intervene between the handling cap 16 made of a plastics and the separator 13 does comprise cams 18, which are formed integral with the inner end surface of the handling cap. The cam mechanism further comprises a base 14 engaging with the cams 18 and driven to move axially and inwards when the cap 16 rotates. Details of this base 14 are the same as those described in the first embodiment.

The discharge mouth comprises a rubber stopper 17 fitted air-tightly and liquid-tightly in the end opening of the cap, so as to keep airtight the downstream end of discharge mouth. An O-ring 19 is interposed liquid-tightly and air-tightly between the downstream end of medicine holding cylinder 15 and the handling cap 16, in order to keep airtight this cylinder against this cap.

Figure 13:
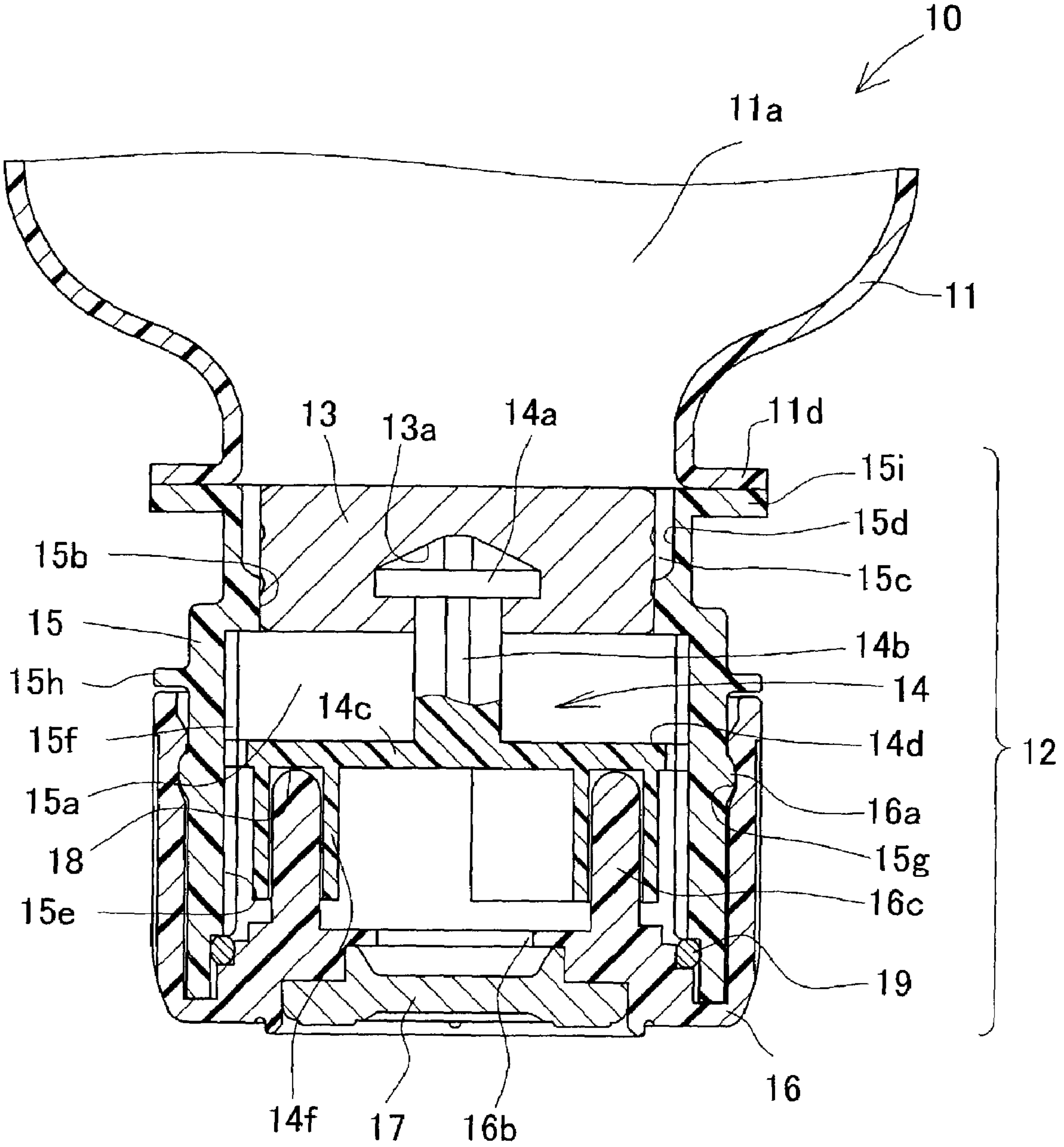
FIG. 13 is an enlarged cross section of a principal part of an infusion vessel provided in a sixth embodiment.

FIG. 13 shows an injection vessel 10 provided in a sixth embodiment of the invention (as set forth in the accompanying claim 5). Structural features, elements as well as functions and effects thereof that are the same as or similar to those in the fifth embodiment are not described here, but being merely indicated by the same reference numerals.

The cam mechanism in this embodiment comprises cam rods 16*c* integrally protruding inwards (upwards in the drawings) from the inner bottom surface of the cap. A base 14 having cams 18 engaging with the tops of cam rods 16*c* is another constituent member of this cam mechanism. Height of each cam 18 changes gradually to make it slanted in angular direction. As the handling cap 16 rotates, the base having the cams 18 engaging with the cap will be forced axially and inwards together with the separator 13 formed integral with this base. Thus, the separator 13 will be moved off the end opening 15*b*, to bring the medium space 11*a* into communication with the medicine chamber 15*a*.

Each cam rod 16*c* is interposed between a radially outer guide wall 14*f* and a radially inner guide wall 14*f*, both the walls protruding axially and outwards (downwards in the drawings) respectively from the radially outer and inner borders of each cam. The recessed region defining and serving as each cam in this embodiment is opened downwards, lest any residual amount of the infusion liquid should remain therein.

In summary, the infusion vessel of the present invention is constructed such that when put into use, the infusion medium can be readily, neatly and smoothly mixed with the medicine to give an infusion liquid to be dosed, thus advantageously preventing foreign matters and bacteria from contaminating any of the medium, medicine and infusion

What we claim is:

1. An infusion vessel comprising:

a vessel body having an internal space in which an infusion medium is reserved, a discharge mouth continuing from a lower portion of the vessel body and having a medicine chamber therein kept airtight against ambient air by a handling cap that is rotatable around a first axis, a separator intervening between the internal space and the medicine chamber so as to keep the chamber in a liquid-tight state against the space, and the separator configured to reposition axially relative to the first axis so as to link the internal space to the medicine chamber, the infusion vessel comprising a cam mechanism comprising an elongate axially extending cam rod that extends in cantilever fashion to an end on one of the handling cap and separator and cam with an axially facing surface on the other of the handling cap and separator, the cam rod spaced from the first axis and having a length that extends generally parallel to the first axis, the cam rod end and axially facing cam surface cooperating by moving against and relative to each other to cause the separator to reposition axially so as to link the internal space to the medicine chamber, as an incident of the handling cap rotating around the first axis.

2. The infusion vessel as defined in claim 1 wherein the discharge mouth has an end opening that is blocked by a stopper and the separator is moved axially inwardly from the end opening as the separator is repositioned so as to link the internal space to the medicine chamber.

3. An infusion vessel comprising:

a vessel body having an internal space in which an infusion medium is reserved, a discharge mouth coninuing from a lower portion of the vessel body and having a medicine chamber therein kept airtight against ambient air, a separator intervening between the internal space and the medicine chamber so as to keep the chamber in a liquid-tight state against the space, and the separator configured to operate so as to link the internal space to the medicine chamber, said infusion vessel further comprising a first rubber stopper configured to be pierced by an instillation needle, the stopper inserted into an external end of the discharge mouth, and the stopper serving to keep airtight the medicine chamber at said end, wherein the discharge mouth comprises a medicine holder having an axis and the medicine chamber formed therein, and a handling cap configured to be rotatable around the axis but incapable of displacement along the axis, the separator comprising a second rubber stopper that is liquid-tightly fitted to an internal open end of the medicine holder, the vessel further comprising a cam mechanism disposed in between the handling cap and the separator and comprising radially spaced, discrete cam elements, so that rotation of the cap causes the cam elements to produce an axial force that causes the second rubber stopper to make an axial movement away from the internal open end, a portion of the cam mechanism residing within the medicine chamber and configured to move axially relative to the discharge mouth.

4. An infusion vessel as defined in claim 3, wherein the first rubber stopper is attached to the handling cap, the cam mechanism comprising a plastics cam and a base, the cam fixed to the first rubber stopper, and the base engaged with the cam so as to be driven axially and inward when the cam rotates in connection with rotational operation of the handling cap, and the separator attached to the base to be removed therefrom in axial direction.

5. An infusion vessel as defined in claim 3, wherein the cam mechanism comprises a cam formed integral with the handling cap and a base engaging therewith to be driven axially and inward when the cam rotates in connection with rotational operation of the handling cap, the separator attached to the base so as not to be removed therefrom in axial direction.

6. An infusion vessel as defined in claim 3, wherein the cam mechanism comprises a base having a cam formed therein and engaging the cap, the separator secured to the base so as not to be removed axially therefrom, such that rotational operation of the cap will cause the base to move axially inward.

7. An infusion vessel comprising:

a vessel body having an internal space in which an infusion medium is reserved, a discharge mouth continuing from a lower portion of the vessel body and having a medicine chamber therein kept airtight against ambient air, a separator intervening between the internal space and the medicine chamber so as to keep the chamber in a liquid-tight state against the space, and the separator configured to operate so as to link the internal space to the medicine chamber, wherein the discharge mouth comprises a medicine holder having an axis and a support member, the medicine holder connected to the support member and configured to be displaced inwardly along the axis, the medicine holder having the medicine chamber flared up outwards in axial direction, the medicine holder comprising a sealing cylinder to liquid-tightly fit on a rubber stopper that defines the separator, the support member fixed axially with respect to the vessel body, the medicine holder configured to move guidingly axially relative to the support member, movement of the medicine holder relative to and towards the support member causes the rubber stopper to move relative to the sealing cylinder towards the flared region of the medicine holder, whereby the medicine chamber communicates with the internal space of the body through the sealing cylinder.

8. An infusion vessel as defined in claim 7, wherein a spacer is detachably attached to an outer periphery of the support cylinder so that: a) with the spacer attached the medicine holder is inhibited from displacement towards the support cylinderfor communication therewith: and b)with the spacer detached the medicine holder can be displaced towards the support cylinder for communication therewith.

9. An infusion vessel comprising:

a vessel body having an internal space in which an infusion medium is reserved, a discharge mouth continuing from a lower portion of the vessel body and having a medicine chamber therein kept airtight against ambient air, a separator intervening between the internal space and the medicine chamber so as to keep the chamber in a liquid-tight state against the space, the separator configured to operate so as to link the internal space to the medicine chamber, wherein the separator comprises a partition and a sealing member, the partition having an aperture for linking the internal space of the body to the medicine chamber, the sealing member causing the aperture to remain closed at its end opened into the internal space, and wherein the discharge mouth comprises a handling cap configured to rotationally operate by movement around an axis and a releaser, the releaser configured to rotate with the handling cap guidingly around the axis and move by rotation around the axis relative to and against the sealing member to thereby deform the sealing member so as to open the aperture at a location where the sealing member is deformed in connection with rotational operation of the cap, so that the thus opened aperture enables communication between the internal space and the medicine chamber.

10. An infusion vessel as defined in claim 9, wherein the releaser is composed of elastic vanes each extending outwards and radially from the axis of the handling cap, and a peripheral wall formed in the partition and having apertures through the wall so that when the handling cap is driven to twist, the vanes in contact with the wall will deform themselves elastically so as to spring into the apertures due to elastic recovery in shape of each blade, thereby opening in part the sealing member.

* * * * *